(12) United States Patent
Azure

(10) Patent No.: US 7,680,543 B2
(45) Date of Patent: *Mar. 16, 2010

(54) TISSUE ABLATION AND REMOVAL

(75) Inventor: Larry Azure, La Conner, WA (US)

(73) Assignee: LaZure Technologies, LLC, La Conner, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/855,977

(22) Filed: Sep. 14, 2007

(65) Prior Publication Data

US 2008/0071262 A1    Mar. 20, 2008

Related U.S. Application Data

(60) Provisional application No. 60/863,484, filed on Oct. 30, 2006, provisional application No. 60/825,660, filed on Sep. 14, 2006.

(51) Int. Cl.
*A61N 1/00* (2006.01)
*A61B 18/18* (2006.01)

(52) U.S. Cl. .................... 607/115; 606/41; 607/116

(58) Field of Classification Search ............. 606/27–31, 606/38–42, 45–50; 607/101, 102, 115, 116; 604/20–22
See application file for complete search history.

(56) References Cited

U.S. PATENT DOCUMENTS

| | | | |
|---|---|---|---|
| 3,991,770 A | 11/1976 | LeVeen |
| 4,016,886 A | 4/1977 | Doss et al. |
| 4,346,715 A | 8/1982 | Gammell |
| 4,448,198 A | 5/1984 | Turner |
| 4,676,258 A | 6/1987 | Inokuchi et al. |
| 4,732,161 A | 3/1988 | Azam et al. |
| 4,763,671 A | 8/1988 | Goffinet |
| 4,821,725 A | 4/1989 | Azam et al. |
| 4,860,752 A | 8/1989 | Turner |
| 5,277,201 A | 1/1994 | Stern |
| 5,370,677 A | 12/1994 | Rudie et al. |
| 5,472,441 A | 12/1995 | Edwards et al. |
| 5,630,426 A | 5/1997 | Eggers et al. |
| 5,681,282 A | 10/1997 | Eggers et al. |
| 5,807,395 A | 9/1998 | Mulier et al. |
| 5,810,804 A | 9/1998 | Gough et al. |
| 5,827,276 A | 10/1998 | LeVeen et al. |
| 5,855,576 A | 1/1999 | Leveen et al. |
| 5,868,740 A | 2/1999 | LeVeen et al. |
| 5,935,123 A | 8/1999 | Edwards et al. |
| 5,957,922 A | 9/1999 | Imran |

(Continued)

OTHER PUBLICATIONS

Aoyagi et al., "Effects of Moderate Hyperthermia on the Rabbit Sacroma Model," *Neurol. Med. Chir.* (Tokyo) 43:105-111 (2003).

(Continued)

*Primary Examiner*—Michael Peffley
(74) *Attorney, Agent, or Firm*—Townsend and Townsend and Crew LLP

(57) ABSTRACT

The present invention provides devices and systems, as well as methods, of electric field delivery and ablation (e.g., non-thermal ablation) of target tissues, including cancerous cells and solid tumors. A method of the present invention can include applying an alternating current to a target tissue and removing ablated or liquefied tissue from the target tissue region.

26 Claims, 22 Drawing Sheets

U.S. PATENT DOCUMENTS

| | | | |
|---|---|---|---|
| 5,968,041 | A | 10/1999 | Edwards |
| 6,050,992 | A | 4/2000 | Nichols |
| 6,071,280 | A | 6/2000 | Edwards et al. |
| 6,090,105 | A | 7/2000 | Zepeda et al. |
| 6,136,020 | A | 10/2000 | Faour |
| 6,148,236 | A | 11/2000 | Dann |
| 6,212,433 | B1 | 4/2001 | Behl |
| 6,231,570 | B1 | 5/2001 | Tu et al. |
| 6,246,912 | B1 * | 6/2001 | Sluijter et al. ............... 607/100 |
| 6,296,638 | B1 * | 10/2001 | Davison et al. ............... 606/41 |
| 6,402,742 | B1 | 6/2002 | Blewett et al. |
| 6,419,653 | B2 | 7/2002 | Edwards et al. |
| 6,440,127 | B2 | 8/2002 | McGovern et al. |
| 6,477,426 | B1 | 11/2002 | Fenn et al. |
| 6,517,534 | B1 | 2/2003 | McGovern et al. |
| 6,537,272 | B2 | 3/2003 | Christopherson et al. |
| 6,682,555 | B2 | 1/2004 | Cioanta et al. |
| 6,738,663 | B2 | 5/2004 | Schroeppel et al. |
| 6,743,226 | B2 | 6/2004 | Cosman et al. |
| 6,850,804 | B2 | 2/2005 | Eggers et al. |
| 6,853,864 | B2 | 2/2005 | Litovitz |
| 6,866,624 | B2 | 3/2005 | Chornenky et al. |
| 6,868,289 | B2 | 3/2005 | Palti |
| 6,939,346 | B2 | 9/2005 | Kannenberg et al. |
| 6,944,504 | B1 | 9/2005 | Arndt et al. |
| 6,958,064 | B2 | 10/2005 | Rioux et al. |
| 6,962,587 | B2 * | 11/2005 | Johnson et al. ............... 606/41 |
| 6,993,394 | B2 | 1/2006 | Eggers et al. |
| 6,994,706 | B2 * | 2/2006 | Chornenky et al. ........... 606/41 |
| 7,016,725 | B2 | 3/2006 | Palti |
| 7,053,063 | B2 | 5/2006 | Rubinsky et al. |
| 7,089,054 | B2 | 8/2006 | Palti |
| 7,135,029 | B2 | 11/2006 | Makin et al. |
| 7,136,699 | B2 | 11/2006 | Palti |
| 7,146,210 | B2 | 12/2006 | Palti |
| 7,238,182 | B2 | 7/2007 | Swoyer et al. |
| 7,311,708 | B2 | 12/2007 | McClurken |
| 7,333,852 | B2 | 2/2008 | Palti |
| 2002/0058933 | A1 | 5/2002 | Christopherson et al. |
| 2002/0077676 | A1 | 6/2002 | Schroeppel et al. |
| 2002/0082610 | A1 | 6/2002 | Cioanta et al. |
| 2003/0130575 | A1 | 7/2003 | Desai |
| 2003/0150372 | A1 | 8/2003 | Palti |
| 2004/0068297 | A1 | 4/2004 | Palti |
| 2004/0087939 | A1 | 5/2004 | Eggers et al. |
| 2004/0116952 | A1 | 6/2004 | Sakurai et al. |
| 2004/0176804 | A1 | 9/2004 | Palti |
| 2005/0171523 | A1 * | 8/2005 | Rubinsky et al. ............... 606/34 |
| 2005/0171574 | A1 | 8/2005 | Rubinsky et al. |
| 2005/0209640 | A1 | 9/2005 | Palti |
| 2005/0209641 | A1 | 9/2005 | Palti |
| 2005/0209642 | A1 | 9/2005 | Palti |
| 2005/0240173 | A1 | 10/2005 | Palti |
| 2005/0240228 | A1 | 10/2005 | Palti |
| 2005/0251126 | A1 | 11/2005 | Gellman et al. |
| 2006/0079883 | A1 | 4/2006 | Elmouelhi et al. |
| 2006/0149226 | A1 | 7/2006 | McCullagh et al. |
| 2006/0149341 | A1 | 7/2006 | Palti |
| 2006/0155270 | A1 | 7/2006 | Hancock et al. |
| 2006/0167499 | A1 | 7/2006 | Palti |
| 2006/0217694 | A1 | 9/2006 | Chin et al. |
| 2006/0217703 | A1 | 9/2006 | Chornenky et al. |
| 2006/0233867 | A1 | 10/2006 | Palti |
| 2006/0237019 | A1 | 10/2006 | Palti |
| 2006/0241547 | A1 | 10/2006 | Palti |
| 2006/0241577 | A1 | 10/2006 | Balbierz et al. |
| 2006/0282122 | A1 | 12/2006 | Palti |
| 2007/0135879 | A1 | 6/2007 | McIntyre et al. |
| 2007/0225766 | A1 | 9/2007 | Palti |
| 2008/0033422 | A1 | 2/2008 | Turner et al. |

OTHER PUBLICATIONS

Baronzio and Hager, "Medical Intelligence Unit—Hyperthermia in Cancer Treatment: A Primer," Landes Bioscience and Springer Science+Business Media LLC; ISBN:0-387-33440-8 (2006).

Chan et al., "Electrically Stimulated Cell Membrane Breakdown in Human Placenta TL and Lung Cancer Cell A549 in 3D Trap Arrays on Si Substate," *Device Research Conference*, pp. 103-104 (Jun. 23-25, 2003).

Chang, D.C., "Design of protocols for electroporation and electrofusion: Selection of electrical parameters," in D. C. Chang, B. M. Chassy, J. A. Saunders and A. E. Sowers. (Ed.Eds.), *Guide to Electroporation and Electrofusion*. Academic Press, Inc., San Diego, pp. 429-455 (1992).

Chang, D.C., "Structure and dynamics of electric field-induced membrane pores as revealed by rapid-freezing electron microscopy," in D. C. Chang, B. M. Chassy, J. A. Saunders and A. E. Sowers. (Ed.Eds.), *Guide to Electroporation and Electrofusion*. Academic Press, Inc., San Diego, pp. 9-27 (1992).

Coss et al., "Effects of Hyperthermia (41.5°) on Chinese Hamster Ovary Cells Analyzed in Mitosis," *Cancer Research* 39:1911-1918 (1979).

Cucullo et al., "Very Low Intensity Alternating Current Decreases Cell Proliferation," *GLIA* 51:65-72 (2005).

DeFord et al., "Effective Estimation and Computer Ccontrol of Minimum Tumour Temperature During Conductive Interstitial Hyperthermia," *Int. J. Hyperthermia* 7:441-453 (1991).

Haemmerich et al., "RF Ablation at Audio Frequencies Preferentially Targets Tumor—a Finite Element Study," *Proceedings of the Second Joint EMBS/BMES Conf.*, pp. 1797-1798 (Oct. 23-26, 2002).

Haemmerich and Wood, "Hepatic Radiofrequency Ablation at Low Frequencies Preferentially," *Int. J. Hyperthermia* 22:563-574 (2006).

Janigro et al., "Alternating Current Electrical Stimulation Enhanced Chemotherapy: a Novel Strategy to Bypass Multidrug Resistance in Tumor Cells," *BMC Cancer* 6:1-12 (2006).

Kirson et al., "Disruption of Cancer Cell Replicatioin by Alternating Electric Fields," *Cancer Res.* 64:3288-3295 (2004).

Kirson et al., "Alternating Electric Fields Arrest Cell Proliferation in Animal Tumor Models and Human Brain Tumors," *PNAS* 104:10152-10157 (2007).

Marmor et al., "Tumor Cure and Cell Survival After Localized Radiofrequency Heating," *Cancer Research* 37:879-883 (1977).

Miller et al., "Cancer Cells Ablation With Irreversible Electroporation," *Technology in Cancer Research & Treatment* 4:1-7 (2005).

Oleson et al., "Biological and Clinical Aspects of Hyperthermia in Cancer Therapy," *Am J. Clin. Oncol.* 11:368-380 (1988).

Pethig, R., "Dielectric Properties of Biological Materials: Biophysical and Medical Applications," *IEEE Trans. EI* 19(5): 453-473 (1984).

Proskuryakov et al., "Necrosis is an Active and Controlled Form of Programmed Cell Death," *Biochemistry* (Moscow) 67:387-408 (2002).

Rubinsky et al., "Irreversible Electroporation: a New Ablation Modality—Clinical Implications," *Tech. Cancer Res. Treatment* 6:1-12 (2007).

Shimm and Gerner, "Hyperthermia in the Treatment of Malignancies," in: Lehman, Justus F., *Therapeutic Heat and Cold* (Maryland, Williams & Wilkins), Ch. 14, pp. 674-699. ISBN 0-683-04908-9 (1990).

Stix, "Blockbuster—New Understanding of the Biology Behind a Successful Cancer Therapy May Lead to a Drug That Can Treat an Array of Solid Tumors," *Scientific American*, pp. 60-63 (May 2006).

Tello et al., "Electrochemical Therapy to Treat Cancer (In Vivo Treatment)," *Proceedings of the 20th Annual International Conference of the IEEE EMBS*, pp. 3524-3527 (Aug. 23-26, 2007).

Yi, "Cellular Ion Content Changes During and After Hyperthermia," *Biochem. Biophys. Res. Communic.* 91:177-182 (1979).

Zimmermann, U., "Electric field-mediated fusion and related electrical phenomena," *Biochim Biophys Acta* 694(3): 227-277 (1982).

Zimmermann, U., et al. "Transcellular ion flow in *Escherichia coli* B and electrical sizing of bacterias," *Biophys. J.* 13(10): 1005-1013 (1973).

Zimmermann, U., et al., "Rotation of cells in an alternating electric field: the occurrence of a resonance frequency," *Z. Naturforsch* [C] 36(1-2): 173-177 (1981).

* cited by examiner

Phase 1

Phase 2

TISSUE ABLATION AND REMOVAL

CROSS-REFERENCES TO RELATED APPLICATIONS

This application claims the benefit under 35 U.S.C. §119(e) of U.S. Provisional Patent Application No. 60/825,660, filed Sep. 14, 2006, and U.S. Provisional Patent Application No. 60/863,484, filed Oct. 30, 2006, the full disclosures of which are incorporated herein by reference.

This application is related to U.S. application Ser. No. 11,855,956, entitled "Device and Method for Destruction of Cancer Cells," filed on Sep. 14, 2007, and U.S. application Ser. No. 11/855,940, entitled "Ablation Probe With Deployable Electrodes," filed on Sep. 14, 2007, both of which are being filed concurrently herewith, the full disclosures of which are incorporated herein by reference.

BACKGROUND OF THE INVENTION

The present invention relates generally to electric field delivery to tissue regions. More specifically, the present invention relates to electric field delivery and non-thermal ablation of target tissue regions, including selective ablation of cancerous cells and solid tumors.

Current tissue ablation techniques rely on a high-frequency, hyper-thermia inducing electric current to the tissue of a patient (e.g., human, animal, etc.) as a means to remove unwanted tissue or lesions, staunch bleeding, or cut tissue. There has been increased interest and activity is the area of hyper-thermal ablation as a tool to treat cancer by heat-induced killing and/or removal of tumor tissue.

In hyper-thermal tumor ablation techniques, high-frequency RF (e.g., "RF thermal ablation") or microwave sources are used to heat tissue resulting in histological damage to the target tissue. In RF thermal ablation techniques, for example, high frequencies, including about 500 kHz and greater, are used to cause ionic agitation and frictional (e.g., resistive) heating to tissue surrounding a positioned electrode. Lethal damage to tissue (e.g., denaturation of tissue proteins) occurs at temperatures in excess of about 47 degrees C., though heat generated near electrodes in RF thermal ablation can reach temperatures up to or exceeding about 100 degrees C.

A number of different cancer ablation methods and devices relying on hyper-thermal ablation or heat-induced tumor tissue destruction have been proposed. One such example includes U.S. Pat. No. 5,827,276, which teaches an apparatus for volumetric tissue ablation. The apparatus includes a probe having a plurality of wires journaled through a catheter with a proximal end connected to the active terminal of a generator and a distal end projecting from a distal end of the catheter. Teachings include a method and probe deployable in a percutaneous procedure that will produce a large volume of thermally ablated tissue with a single deployment.

U.S. Pat. No. 5,935,123 teaches an RF treatment apparatus including a catheter with a catheter lumen. A removable needle electrode is positioned in the catheter lumen in a fixed relationship to the catheter. The treatment apparatuses are taught as being used to ablate a selected tissue mass, including but not limited to a tumor, or treat the mass by hyperthermia. Tumor sites are treated through hyperthermia or ablation, selectively through the controlled delivery of RF energy.

Numerous other methods and devices are taught using hyper-thermal or heat-induced cancer tissue destruction. However, a significant limitation of RF induced, hyper-thermal ablation is the difficulty of localizing the heat-induced damage to targeted cancerous tissue while limiting histological damage and destruction to surrounding healthy, non-target tissue.

Thus, there is a need for minimally invasive ablation techniques that selectively destroy cancerous cells while minimizing damage to healthy tissue.

BRIEF SUMMARY OF THE INVENTION

The present invention provides systems, devices and related methods for applying electric fields for cancerous cell destruction and tissue ablation, e.g., non-thermal tissue ablation. Devices of the present invention will generally be designed to advance an electrode or plurality of electrodes to a target tissue region and apply an electric field to the target tissue region. The electrode or plurality thereof can be positioned such that the applied electric field radiates throughout the target tissue region, including, for example, where the electric field radiates outwardly and in a plurality of directions radially through the target tissue. Additionally, the energy applied to the target tissue region can be selected such that electrically generated heat is minimized and elevations in tissue temperature can be avoided. In particular embodiments, the applied electric field is generally a low-intensity (e.g., less than about 50 V/cm) and intermediate frequency (e.g., between about 50 kHz and 300 kHz) alternating current field sufficient to provide low-power or non-thermal ablation of target cells. The electrode positioning and application of the electric field (e.g., low-power/non-thermal ablative electric field) of the present invention has demonstrated to be surprisingly effective in ablating cancerous cells can occur without a thermal effect being a factor in the ablation process. Moreover, the ablative process according to one embodiment of the present invention primarily occurs among abnormally proliferating cells or cells exhibiting unregulated growth (e.g., cancerous cells). Thus, the present invention provides the additional advantage of providing minimally invasive, selective ablation or destruction of cancerous cells, while leaving normal cells or tissue substantially intact.

In one aspect, the present invention includes methods of destroying cancerous cells of a tissue. Such a method includes applying an alternating current to a target tissue and removing liquefied tissue from the target tissue region. Methods of delivering an electric field to a tissue and destroying cancerous cells are also provided. Such a method includes positioning an electrode within a target tissue region comprising cancerous cells and applying an alternating electrical current to the target tissue so as to non-thermally ablate cancerous cells of the target tissue, and removing ablated tissue from the target tissue region. In another embodiment, a method includes advancing a probe comprising a plurality of electrodes to a target tissue region comprising cancerous cells, and deploying the plurality of electrodes to at least partially define an ablation volume. The method can additionally include applying an alternating current to the ablation volume to destroy cancerous cells within the volume, and removing liquefied tissue from the target tissue region.

The present invention further includes devices, including those for delivering an electric field to a tissue to destroy cancerous cells therein. In one embodiment, a device includes a probe having one or a plurality of electrodes positionable at a target tissue region; and a tissue removal member for removing ablated tissue from the target tissue region. Systems for destroying cancerous cells of a tissue are also provided. A system can include a probe having electrode(s) positionable at a target tissue region, an energy source coupled to the prove to provide electrical current to ablate cancerous cells of the target tissue, and a removal unit configured for removing tissue from the target tissue.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIGS. 15A and 15B show a cross-sectional, front view and side view, respectively, of a probe including microcatheters with deployable electrodes. FIGS. 15C and 15D show a first phase and a second phase of deployment, respectively.

DETAILED DESCRIPTION OF THE INVENTION

The present invention provides systems and devices, and related methods for low-power or non-thermal tissue ablation. According to the present invention, an electrode or plurality of electrodes can be introduced into a target tissue region and an electric field applied to the target tissue region. The energy applied to the target tissue region can be selected such that electrically generated heat is minimized and rises in tissue temperature can be avoided, thereby providing low-power or non-thermal ablation of target cells. Devices and methods of the present invention have been demonstrated to be effective in ablating cancerous cells without a thermal effect being a factor in the ablation process, with ablation occurring primarily among abnormally proliferating cells or cells exhibiting unregulated growth (e.g., cancerous cells). Thus, the present invention is advantageous in providing minimally invasive, selective ablation or destruction of cancerous cells, while leaving normal cells or tissue substantially intact.

In one embodiment, the target tissue region includes a mass or solid portion of tissue. Typically, the target tissue region includes cancerous cells including, for example, a target tissue region including a solid tumor. The volume of the tissue to be subject to the inventive methods can vary, and will depend at least partially based on the size of the mass of cancerous cells. Peripheral dimensions of the target tissue region can be regular (e.g., spherical, oval, etc.), or can be irregular. The target tissue region can be identified and/or characterized using conventional imaging methods, and various imaging systems can be used for locating and/or positioning of a device or electrodes of the invention within a patient's tissue or at or within a target tissue region.

Electrodes can be positioned as described and an alternating electric field applied. Ablation techniques according to the present invention can be accomplished in some embodiments without an increase in local tissue temperature and without thermal effects of energy application being a primary means by which tissue ablation occurs. The applied electric field can include a low-intensity, intermediate frequency alternating current. In some embodiments, electrode configuration and field application can take advantage of tumor physiology, including, e.g., orientation of dividing/proliferating cells within a target tissue region, and ensure that the electric field provided is substantially aligned with a division axis of a dividing cancerous cell.

Figure 1:
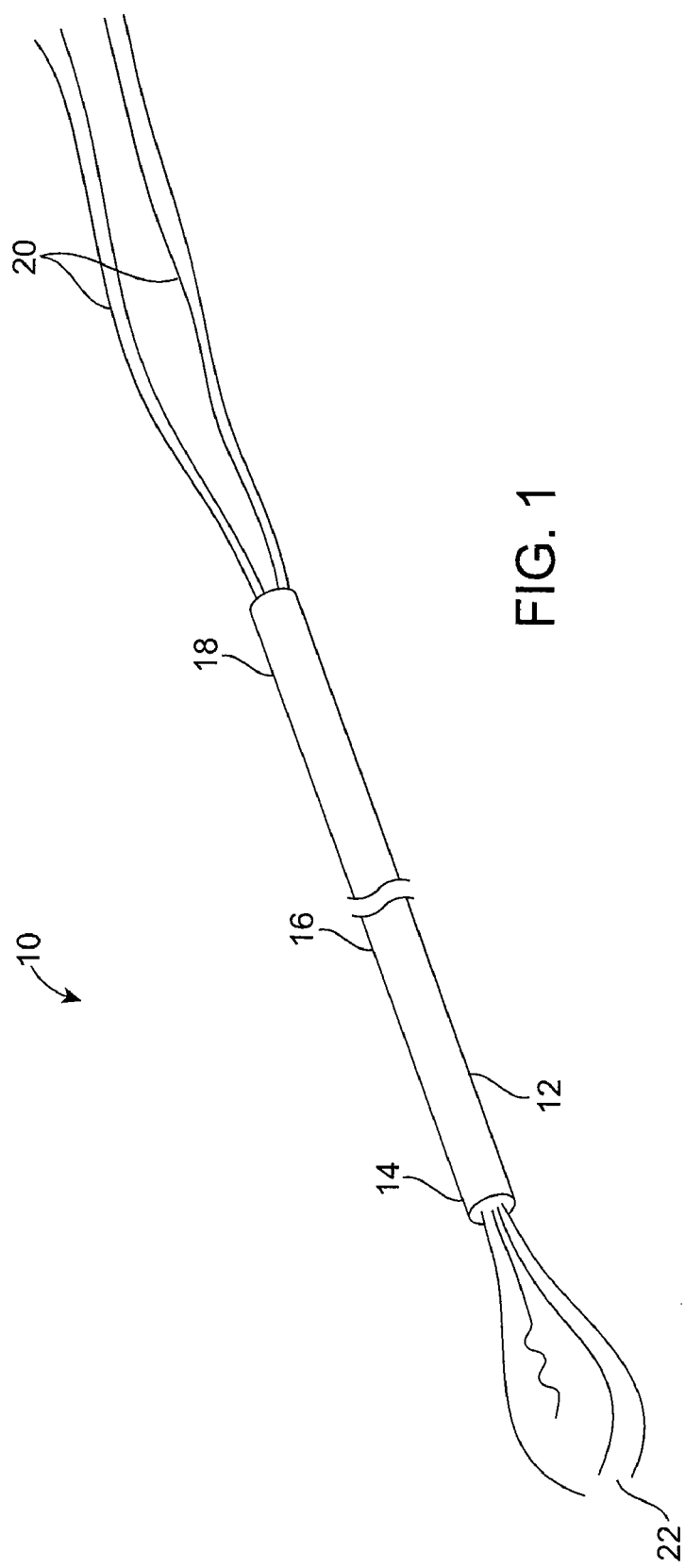
FIG. 1 illustrates a device according to an embodiment of the present invention.

Referring to FIG. 1, a device according to an embodiment of the present invention is described. The device 10 includes a delivery member 12 having a distal portion 14 and a proximal portion 16. The device 10 further includes a proximal portion 18 of the device that can be coupled (e.g., removably coupled) to the delivery member 12. Additionally, the device 10 can include conductive cables 20 electrically coupled to an energy source (not shown). The device includes a plurality of electrodes 22 at the distal portion 14 of the delivery member 12. The electrodes 22 can be positioned or fixed, for example, at the distal end of the delivery member 12 or positionable and deployable from a lumen of the delivery member 12 and retractable in and out of the distal end of the delivery member 12. The electrodes 22 can include a non-deployed state, where the electrodes 22 can be positioned within a lumen of the delivery member 12, and a deployed state when advanced from the distal end of the delivery member 12. Electrodes 22 are advanced out the distal end and distended into a deployed state substantially defining an ablation volume.

The present invention can include a variety of electrode compositions, configurations, geometries, etc. In certain embodiments, electrodes can include tissue-penetrating electrodes including, for example, small diameter metal wires having tissue-piercing or sharpened distal ends that can penetrate tissue as they are advanced within the target tissue region. Electrodes can be non-insulated or can include an insulated portion. In one embodiment, a non-insulated portion of the electrode provides an electric field delivery surface for delivery of electrical current to the surrounding tissue. Electrodes can be substantially rigid, e.g., so as to be more easily advanced through tissue, including hardened or more dense tissue, or can be more flexible, depending upon the desired use. In one embodiment, an electrode includes a needle or needle-like electrode or electrode having a substantially linear portion. In another embodiment, electrodes can be curved, having a curved portion or portion with a radius of curvature. Electrode composition can vary and in certain embodiments can include a memory metal (e.g., commercially available memory metals, Nitinol™, etc.) or sprung steel. Suitable electrode materials can include, e.g., stainless steel, platinum, gold, silver, copper and other electrically conductive materials, metals, polymers, etc. In certain embodiments, electrodes can be positioned in and deployable from a lumen of a catheter and/or microcatheter or other member for introducing the electrode into a tissue.

In another embodiment, the present invention can make use of one or more sensor mechanisms to provide feedback and/or control the ablation process. Sensor mechanisms can include sensors or detectors that detect and measure parameters such as temperature, current, voltage, impedance, pH and the like. Certain embodiments of the present invention can include modifying the applied electric current at least partially based on a detected characteristic or a change in a detected characteristic. In one embodiment, for example, modification of the applied electric current can occur in response to a measured temperature, impedance, and the like. Modification can include, for example, modifying the voltage, frequency, etc. of the applied current and/or discontinuing application of the electric current, for example, where the ablation process or a stage thereof is determined to be completed.

A target tissue region can be located anywhere in the body where the tissue ablation methods of the present invention would be desired or beneficial. Target tissue is not limited to any particular type and non-limiting examples can include, e.g., breast tissue, prostate tissue, liver, lung, brain tissue, muscle, lymphatic, pancreatic tissue, colon, rectum, bronchus, and the like. The target tissue region will typically include a mass or solid portion of tissue. Typically, the target tissue region includes cancerous cells including, for example, a target tissue region including a solid tumor. The term "cancerous cell", as used herein, generally refers to any cells that exhibit, or are predisposed to exhibiting, unregulated growth, including, for example, a neoplastic cell such as a premalignant cell or a cancer cell (e.g., carcinoma cell or sarcoma cell), and are amenable to the ablation methods described herein. The volume of the tissue to be subject to the inventive methods can vary depending, for example, on the size and/or shape of the mass of cancerous cells, as well as other factors. Peripheral dimensions of the target tissue region can be regular (e.g., spherical, oval, etc.), or can be irregular.

Imaging systems and devices can be included in the methods and systems of the present invention. For example, the target tissue region can be identified and/or characterized using conventional imaging methods such as ultrasound, computed tomography (CT) scanning, X-ray imaging, nuclear imaging, magnetic resonance imaging (MRI), electromagnetic imaging, and the like. In some embodiments, characteristics of the tumor, including those identified using imaging methods, can also be used in selecting ablation parameters, such as energy application as well as the shape and/or geometry of the electrodes. Additionally, these or other known imaging systems can be used for positioning and placement of the devices and/or electrodes in a patient's tissues.

As set forth above, the electrode is positioned within the target tissue region and the applied electric field is sufficient to provide low-power or non-thermal ablation of target cells. The term "non-thermal ablation" as used herein generally refers to techniques of the present invention including the removal of or destruction of the function of tissue or cells of a tissue by application of an electric field, and where the energy application/delivery process occurs without a substantial increase in local tissue temperature and without thermal effects of energy application being a significant or primary means by which tissue ablation occurs. In many embodiments, an increase in local tissue temperature can be avoided altogether, with no resulting increase in temperature being detectable in the target tissue region. In some embodiments, however, small changes/elevations in temperature in the target tissue region may occur, but will typically be no more than a few degrees C. above body temperature (e.g., less than about 10 degrees C., but typically no more than about 2 degrees above body temperature), and without the thermal effects being the primary means by which tissue ablation occurs (e.g., no significant thermally-mediated, lethal protein denaturation). Typically, the applied electric field includes a low-intensity, intermediate frequency alternating current. The intermediate frequency employed according to the present invention, for example, will be less than that typically required for frictional/resistance heating to tissue surrounding the electrode (e.g., less than about 400 kHz, preferably about 300 kHz or less). In one embodiment, for example, the electric current provides a voltage field less than about 50 V/cm. In another embodiment, the electrical current includes a frequency between about 50 kHz and about 300 kHz.

The voltage field and/or the frequency and/or the magnitude of the applied current can be held constant during energy application or varied. One or more treatment phases can be applied, with each phase having selected treatment parameters (e.g., energy parameters, duration, etc.). In some embodiments, providing a non-constant or varying voltage and/or frequency and/or current by "scanning" across a given range may be desired, for example, to ensure that the optimal ablative voltage/frequency/current is applied to the target tissue region. In another embodiment, a particular voltage and/or frequency and/or current can be selected prior to energy application. Furthermore, the electrode(s) can be positioned within the target tissue region such that electrical current application occurs from within the target tissue, and the target tissue is ablated from the inside out. In one embodiment, electrode(s) are positioned within the target tissue region (e.g., tumor) and the applied electrical current provides an electric field extending radially outward from the electrode. In certain embodiments, such positioning can take advantage of tumor physiology, including, e.g., orientation of dividing/proliferating cells within a target tissue region, and ensure that the electric field provided by the electrode is substantially aligned with a division axis of a dividing cancerous cell.

Figure 2C:
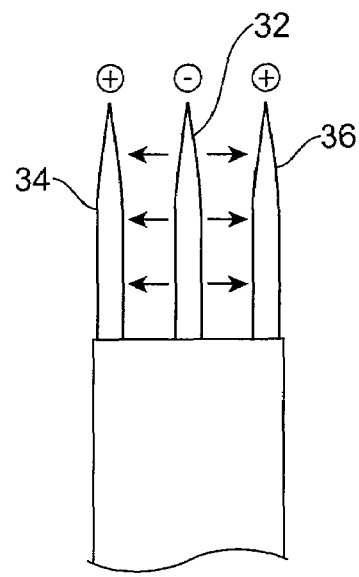
FIGS. 2A through 2C illustrate a device according to another embodiment of the present invention.
Figure 2A:
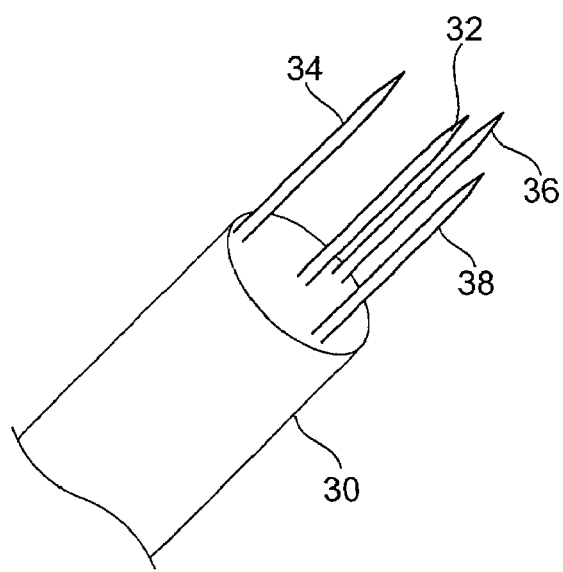
Figure 2B:
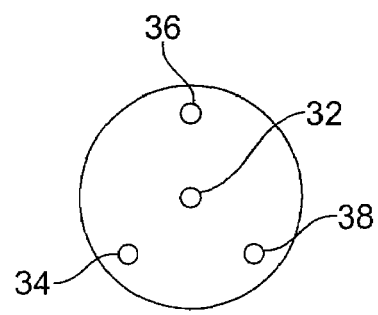

FIGS. 2A through 2C show a device having a plurality of electrodes according to another embodiment of the present invention. As shown, the device 30 includes a plurality of electrodes extending from the distal portion of the device.

FIG. 2A shows a three dimensional side view of the device having the plurality of electrodes. FIG. 2B shows a top view of the device illustrating the electrode arrangement. The plurality includes a centrally positioned electrode 32 and outer electrodes 34, 36, 38 spaced laterally from the central electrode 32. The illustrated electrodes include substantially linear needle-like portions or needle electrodes. The electrodes extend from the distal portion of the device and are oriented to be substantially parallel with the longitudinal axis of the device 30. Additionally, each electrode is substantially parallel with other electrodes of the plurality. The plurality of electrodes substantially define the ablation volume, with the outer electrodes 34, 36, 38 substantially defining a periphery of the ablation volume and the electrode 32 positioned within or at about the center point of the defined periphery. Each of the electrodes can play different roles in the ablation process. For example, there can be changes in polarity and/or polarity shifting between the different electrodes of the device. As with other devices of the invention, electrodes can be electrically independent and separately addressable electrically, or two or more electrodes can be electrically connected, for example, to effectively function as one unit. In one embodiment, for example, outer electrodes 34, 36, 38 can be electrically connected and, in operation, include a polarity different from that of the inner electrode 32. As illustrated in FIG. 2C the electrodes 32 and 34, 36 of the device can include opposing charges (e.g., bipolar). In such an instance, the applied electrical current can provide an electrical field, as illustrated by the arrows, extending radially outward from the central electrode 32 and toward the peripherally positioned or outer electrode(s) 34, 36.

In some embodiments, devices and/or systems of the present invention include electrically floating systems or systems designed to operate without an earth grounding. In some instances, it was observed that electrode configurations that were electrically floating in this manner allowed more accurate or controllable field application and/or delivery. The low-power requirements of systems according to certain embodiments allow more design options (e.g., battery operation) in configuring devices and systems that are electrically floating, as described, compared, for example, to known techniques such as thermal RF or microwave ablation, or high-voltage irreversible electroporation that require much higher powered energy delivery and corresponding power sources.

Figure 3A:
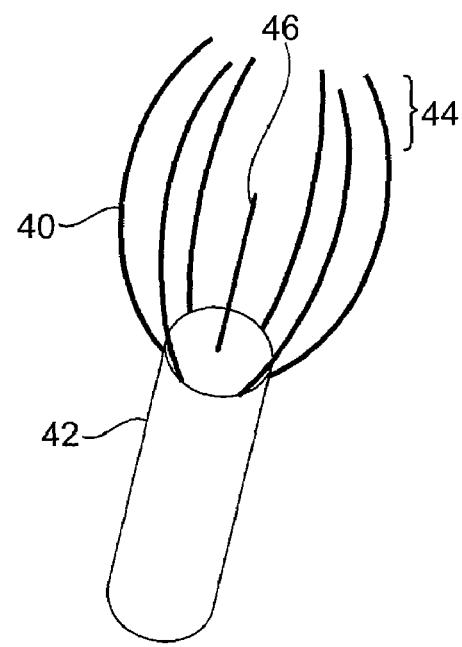
FIGS. 3A and 3B show a device having an electrode configuration according to an embodiment of the present invention.
Figure 3B:
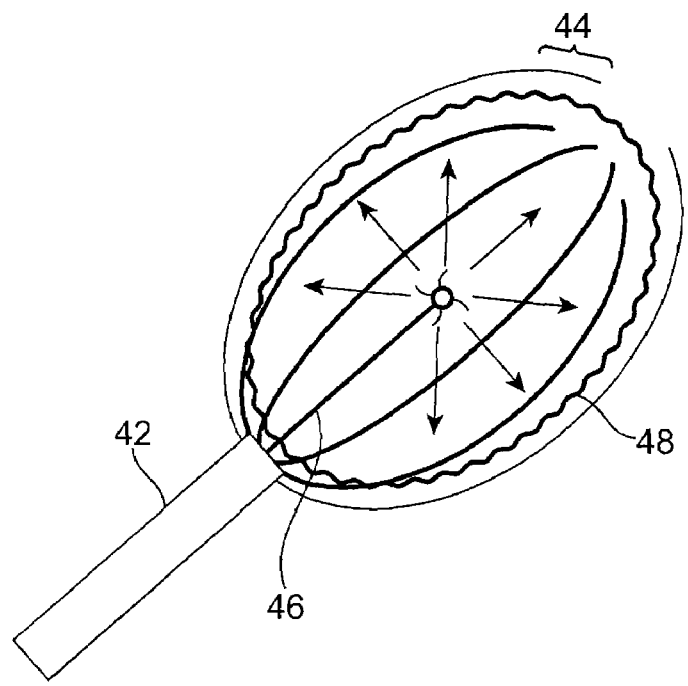

Another embodiment of a device of the invention is described with reference to FIGS. 3A and 3B. The device 40 includes a plurality of electrodes at or extending from the distal end 42 of the device 40. The plurality of electrodes includes outer positioned electrodes 44 that are curved and substantially define an ablation volume. An electrode 46 is positioned within the volume defined by the outer electrodes 44 and spaced from the electrodes 44. The central electrode 46 is shown as being substantially linear and parallel with the longitudinal axis of the device 40, although other configurations will be available. FIG. 3B shows a target tissue 48 within the periphery defined by the outer electrodes 44 with an electrical current being applied to the target tissue 48, and illustrating an oblong or oval ablation volume being defined by the curved electrodes 44. Thus, a target tissue region 48, such as a solid tumor, can essentially be encased within the volume defined by the outer electrodes 44. Arrows illustrate an electric field extending outward and radially from the electrode 46 and in a plurality of different directions.

Figure 4:
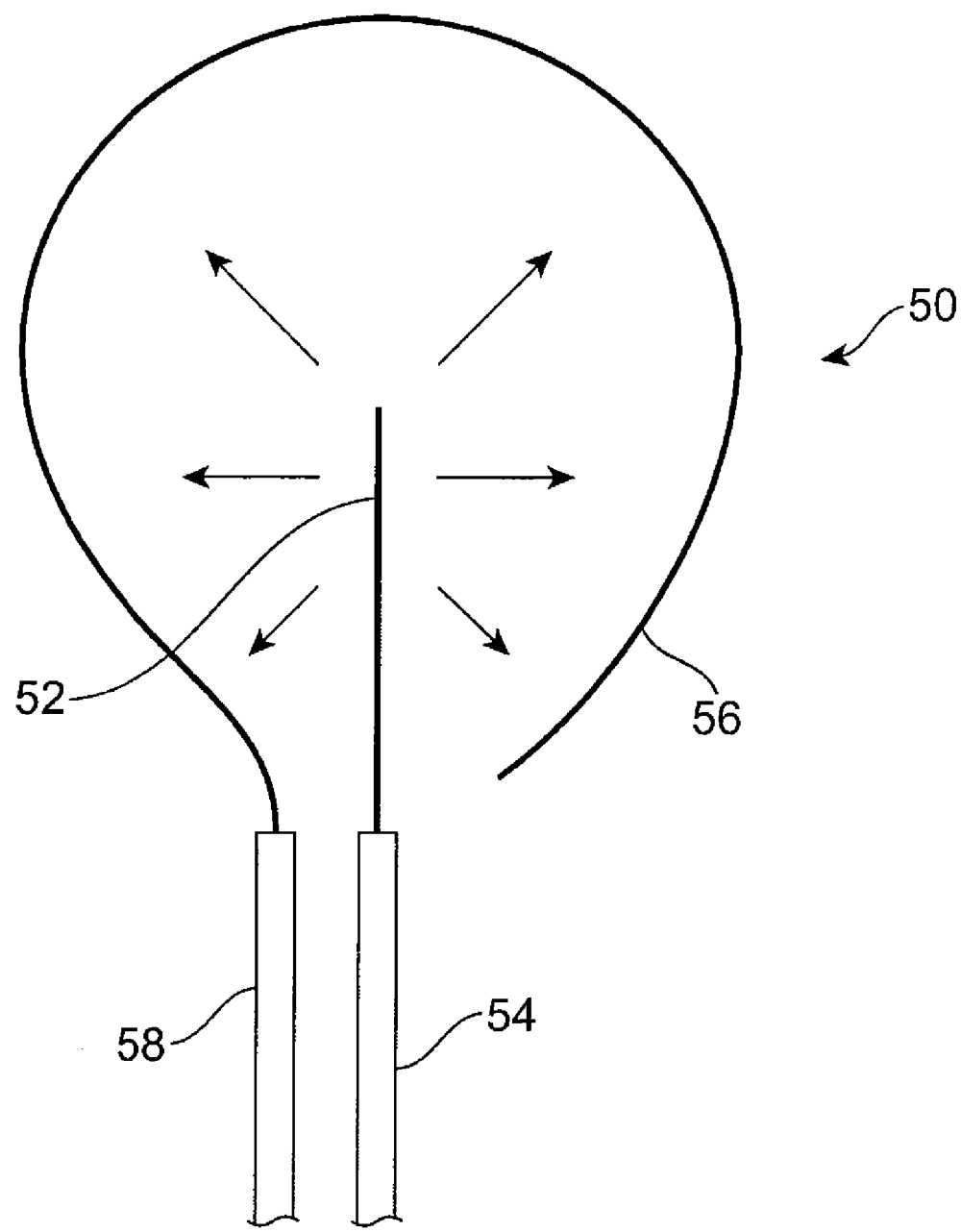
FIG. 4 illustrates an electrode arrangement according to an embodiment of the present invention.

Electrodes of a device according to another embodiment of the present invention are described with reference to FIG. 4. The device 50 includes a substantially linear electrode 52 that is retractable in and out of a microcatheter 54 and an electrode 56 having a curved portion, the electrode retractable in and out of a microcatheter 58. Microcatheters 58 and 54 can be included in a single delivery member, such as in a lumen(s) of a delivery catheter or can be independently arranged, e.g., for individually accessing and addressing a target tissue. One outer electrode is illustrated (e.g., electrode 56), though multiple outer or secondary electrodes can be provided, as illustrated in other embodiments (e.g., see below).

Figure 5A:
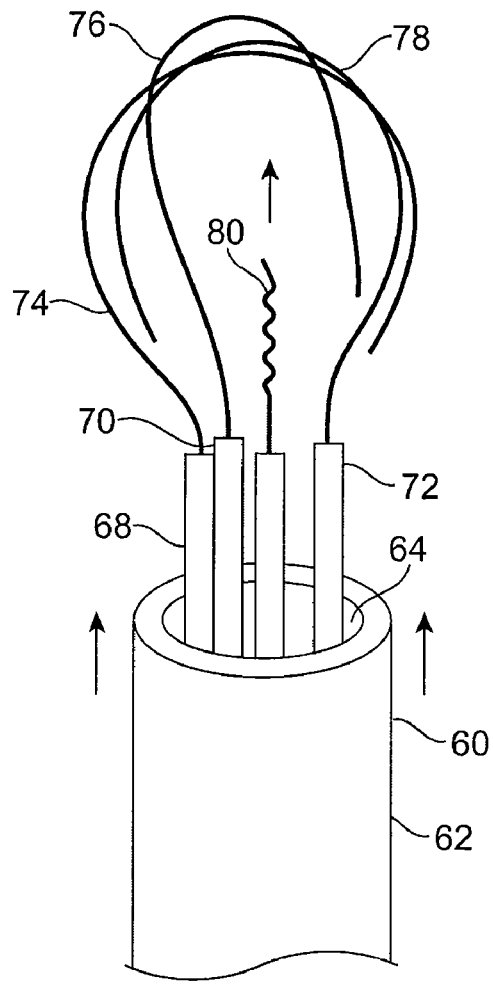
FIGS. 5A and 5B illustrate a catheter and microcatheter device according to another embodiment of the present invention.
Figure 5B:
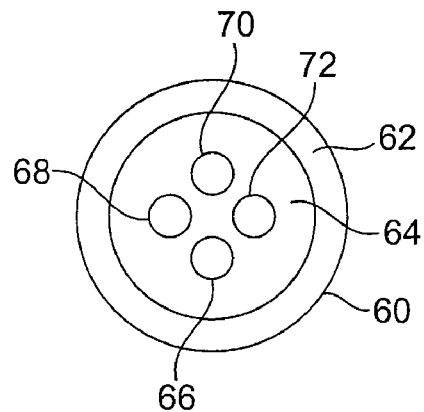

A device can include a plurality of electrodes, each deployable or retractable in and out of a microcatheter, with each microcatheter/electrode assembly optionally positioned within a central lumen of a larger delivery member, as illustrated in FIGS. 5A and 5B. The device 60 includes a delivery member 62 with a lumen 64, and microcatheters 66, 68, 70, 72 positioned in the lumen. FIG. 5B shows a top view of the device with microcatheters 60, 68, 70, 72 positioned in the lumen 62 of the delivery member 60. Electrodes 74, 76, 78 each having a curved portion, are deployable from microcatheters 68, 70, 72 and, in a deployed state, substantially define an ablation volume. Electrode 80 is deployable from microcatheter 66 is positioned within the ablation volume substantially defined by electrodes 74, 76, 78.

Figure 6A:
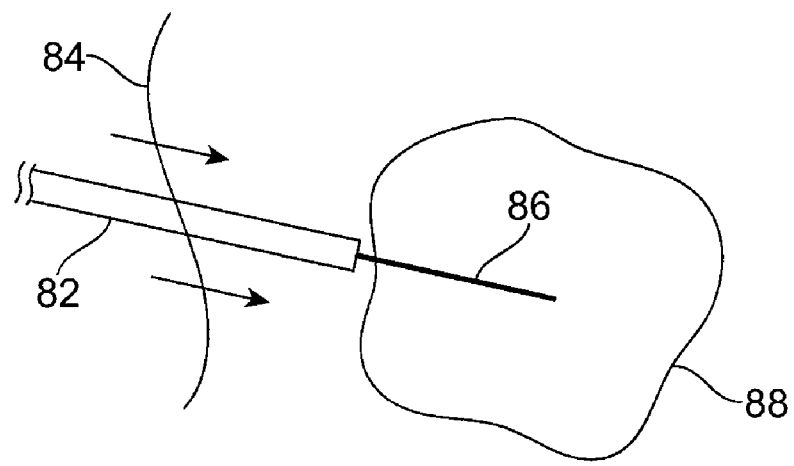
FIGS. 6A and 6B illustrate a method according to an embodiment of the present invention.
Figure 6B:
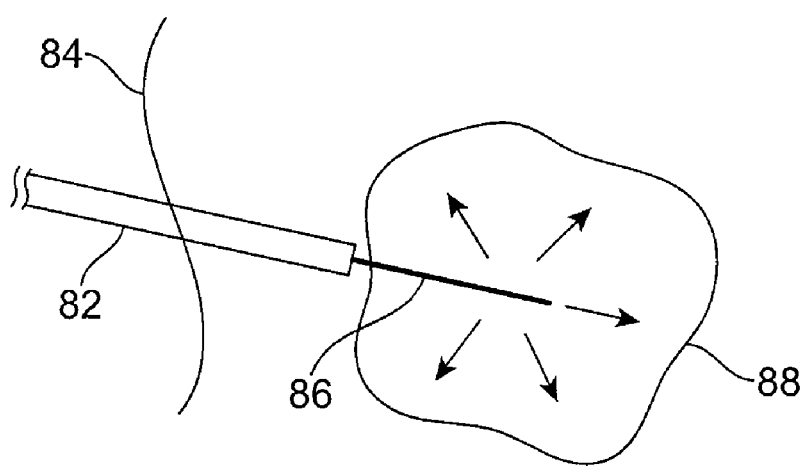
Figure 7A:
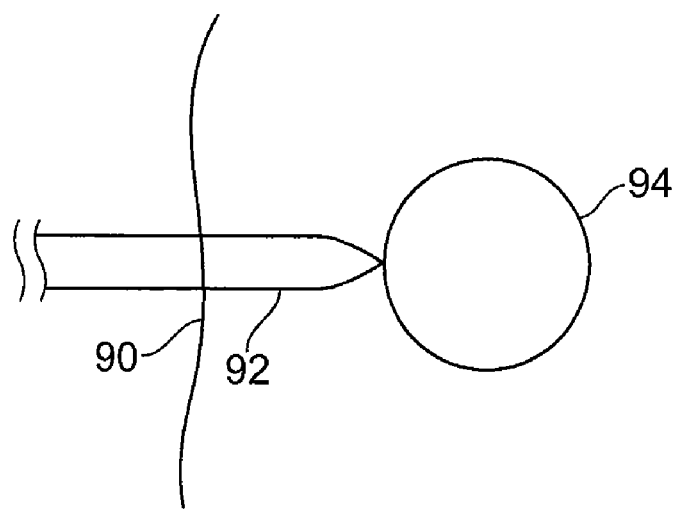
FIGS. 7A and 7B illustrate a method according to another embodiment of the present invention.
Figure 7B:
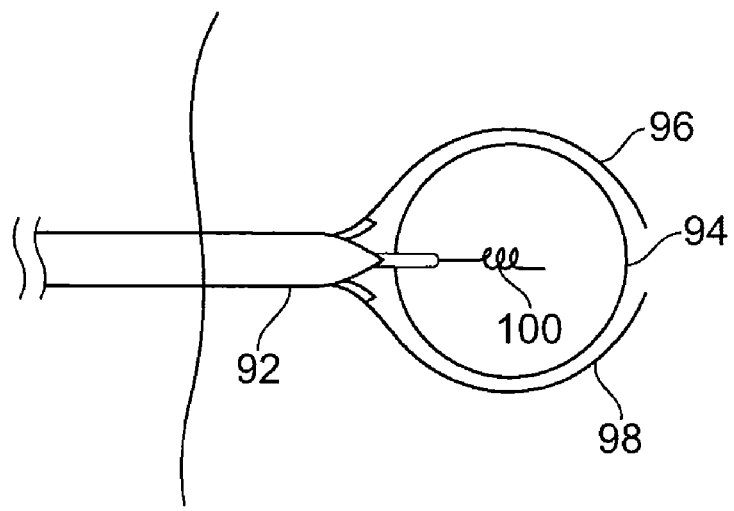

In use, as shown in FIG. 6, a device 82 of the present invention can be advanced through the patient's tissue 84, and an electrode 86 of the device 82 positioned within a target tissue region 88 (e.g., tumor). Once the electrode is positioned in the target tissue region 88, electrical current is delivered to the target tissue region 88. As the electrode 86 is positioned within the target tissue region 88, the applied electrical current can provide an electric field that radiates outward and in a plurality of directions. A system or device of the invention can be operated in monopolar mode or bipolar mode. In one monopolar operation embodiment, a second electrode can be placed, for example, outside the patient's body, such as by positioning the patient on a conductive pad or plate (e.g., metal plate) and may make use of conductive materials, such as conductive gels or adhesives, placed between the patient's skin and the second electrode. In a bipolar mode embodiment, outer electrodes substantially defining an ablation volume can function as return electrodes, or complete a circuit with an electrode(s) positioned within the ablation volume, with applied current flowing through tissue of the target region positioned between the outer electrodes and electrode(s) positioned within the ablation volume. FIG. 7 shows use of a device of the present invention according to another embodiment of the present invention. As described above, the device 90 is advanced through the patient's tissue and the delivery member 92 positioned proximate to the target tissue region 94. Once the delivery member 92 is positioned, a plurality of electrodes 96, 98, 100 can be deployed from the delivery member 92. Outer electrodes 96, 98 are deployed within or around the perimeter of the target tissue region 94, e.g., at about the margin of the target tissue region (e.g., tumor margin) and substantially define the ablation volume or target region. The inner electrode 100 is positioned within the ablation volume.

The present invention can include various means of accessing or addressing a target tissue and positioning electrodes/probes for delivery of the described ablative treatment. Typically, positioning of a device of the invention will include a minimally invasive access and positioning techniques, including, e.g., access techniques commonly used with other types of tissue ablation (e.g., thermal RF ablation, microwave ablation, high-voltage electroporation, and the like). For example, devices of the invention can be introduced percutaneously through the skin and advanced through tissue and positioned at a target tissue. Though, addressing a target tissue and positioning of a device can occur in conjunction with more conventional surgical techniques or laparoscopic techniques.

Figure 8A:
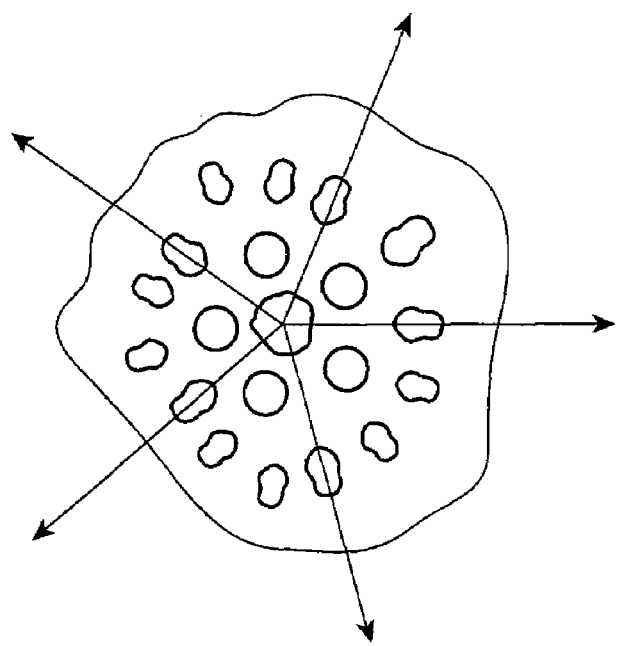
FIGS. 8A and 8B illustrate a tumor or mass of cancerous cells, with FIG. 8B showing a focused view of a dividing cancerous cell.
Figure 8B:
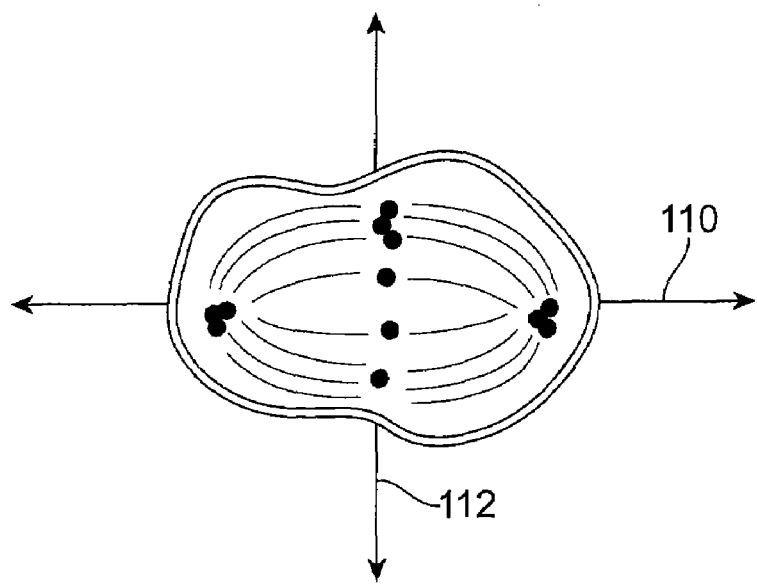

As set forth above, certain embodiments of the present invention include positioning of an electrode within the target tissue region and applying an alternating electrical current, with the applied electrical current providing an electrical field that radiates outwardly from the positioned electrode. Electric field application in this manner was found to be highly effective in disrupting and destroying cancerous cells via low-power ablation and in the absence of a thermal ablative effect. In certain embodiments, disruption of cancerous cells and resulting ablation according to the present invention even more effectively occurred where the electrical field provided by an electrode of an inventive device was substantially aligned with a division axis of a dividing cancerous cell or plurality of cells. FIG. 8A shows a simplified version of a growth pattern and physiology of a cancer tumor or solid mass of cancerous cells, illustrating tumor growth by cancer cells dividing outwardly from the center of a region. Arrows indicate division axes of cancerous cells dividing outwardly from the center. FIG. 8B shows a focused and simplified view of a dividing cell of the tumor of FIG. 8A, further illustrating the concept of an axis of cell division. The illustrated dividing or proliferating cancerous cell (illustrated at a metaphase stage of mitosis) includes an axis of cell division 110 substantially orthogonal to a metaphase plate axis 112, where the cell divides substantially along the plate axis 112 and cell proliferation and growth occurs along the cell division axis 110. Thus, in certain embodiments of the invention, the positioning of an electrode within a tissue region, e.g., proximate to the center region of a tumor or mass of cancer cells, and/or the configuration and arrangement of the electrodes of the device, can be selected such that the electrical field radiates outwardly from about the center region and the electric field is substantially aligned with the division axes of cells of the growing tumor.

Furthermore, the electric field application as described was observed to be particularly effective in selectively disrupting and destroying the dividing cancerous cells, while having little or no effect on normal cells that were not exhibiting unregulated growth and proliferation. Without being bound by any particular theory, electric field application as described may specifically disrupt the cell division process (e.g., mitosis) or progression through the cell cycle, or a stage or process thereof (e.g., mitotic spindle formation, microtubule polymerization, cytoplasmatic organelle function or arrangement, cytokinesis, cellular osmotic balance or the like) and, therefore, more particularly effects cells exhibiting unregulated growth (e.g., cancerous cells) and progressing more rapidly through the cell cycle.

According to the present invention, a target tissue region can be ablated in whole or in part. It will be recognized that while it is generally desirable to ablate as much of the target region or tumor as possible, in some embodiments, methods can include ablation of a portion or less than the entirety of the target region. In some instances, partial tumor ablation can be sufficient to ultimately destroy or kill an entire tumor or cancerous tissue region.

Figure 9A:
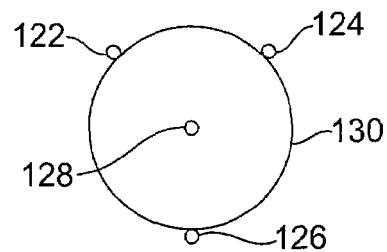
FIGS. 9A through 9D show a device and method according to an embodiment of the present invention.
Figure 9B:
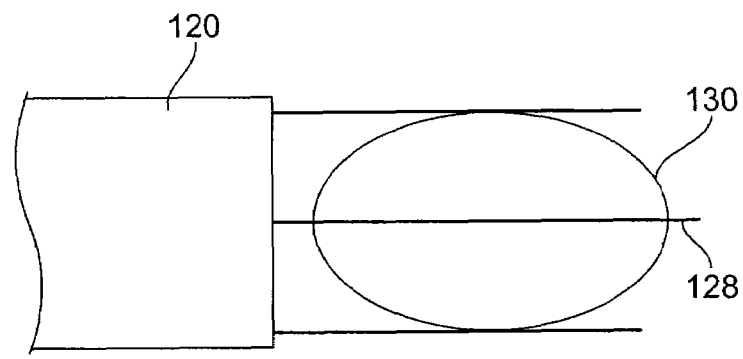
Figure 9C:
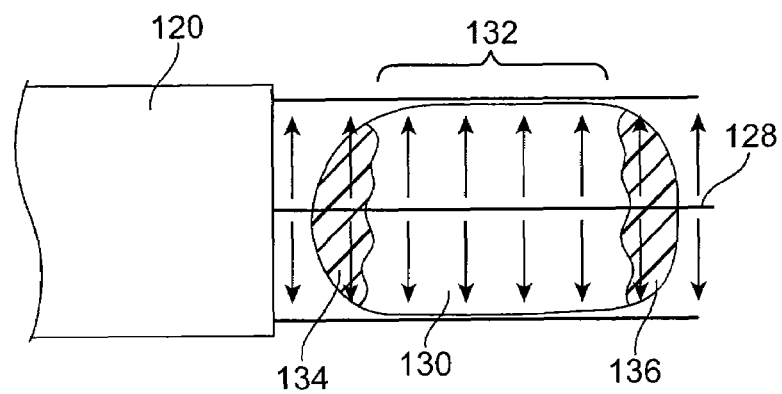
Figure 9D:
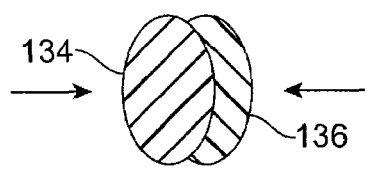

Use of a device according to an embodiment of the invention (e.g., the device of FIGS. 2A through 2C) is discussed with reference to FIGS. 9A through 9D. The device 120 includes a plurality of electrodes, including outer electrodes 122, 124, 126 substantially defining an ablation volume and at least one inner electrode 128. The device can be positioned at a target tissue region including a tumor or portion thereof. The tumor 130 is shown positioned substantially within the ablation volume, with the inner electrode 128 positioned about through the center of the tumor and outer electrodes 122, 124, 126 spaced laterally from the inner electrode 128 and positioned at about or slightly inside or outside the tumor margin. FIG. 9A shows a top sectional view of the tumor 130 and positioned electrodes 122, 124, 126, 128, and FIG. 9B shows a side view of the same. An electric field, illustrated by the arrows in FIG. 9C, is provided by the positioned electrodes and the application of an electrical current. As can be seen, in the parallel straight needle electrode configuration shown in FIGS. 9A through 9C, the electrical field along the length of the ablation volume is oriented in a direction orthogonal to the longitudinal axis of the device. The electric current emanating from the center electrode 128 toward the outer electrodes 122, 124, 126 provides a field that is substantially aligned with the direction of cell division for many of the tumor cells, particularly those in region 132, which divide in a direction from the tumor center and outward (see, e.g., FIGS. 8A and 8B). It will be recognized that arrows are provided for illustrative purposes, and that embodiments of the invention are not limited to any particular current and/or electrical field direction, but may include directions other than and/or in addition to those specifically illustrated. The tumor includes region 132 where direction of tumor cell division is believed more closely aligned with the electrical field. In the illustrated configuration, the tumor can include regions 134, 136 at opposing ends of the tumor that may include a greater proportion of cells having cell division axes not in alignment with the provided electric field, or, in other words, are at an angle relative to the electric field and may remain alive following application of energy, while a greater proportion of cells of region 132 are ablated. However, in one example, using tumor ablation in this manner, the tissue/cells of region 132 were ablated and materials subsequently removed from the treatment site (e.g., squezzed out by application of pressure) and/ or absorbed by surrounding tissue, and regions 134 and 136 were observed to collapse inward forming a flat, "pancake-like" tissue residue (FIG. 9D), which eventually died subsequent to energy application. Remarkably, numerous experimental (e.g., animal) models that were subject to the described ablation techniques of the present invention demonstrated complete remission of detectable tumor. These results indicated that the present inventive methods effectively ablate tumor tissue, can destroy a solid tumor, even where less than the entirety of tumor tissue is ablated, and illustrated the improved tissue ablation where the electric field is aligned with the direction of cell division of cancerous cells.

Figure 10:
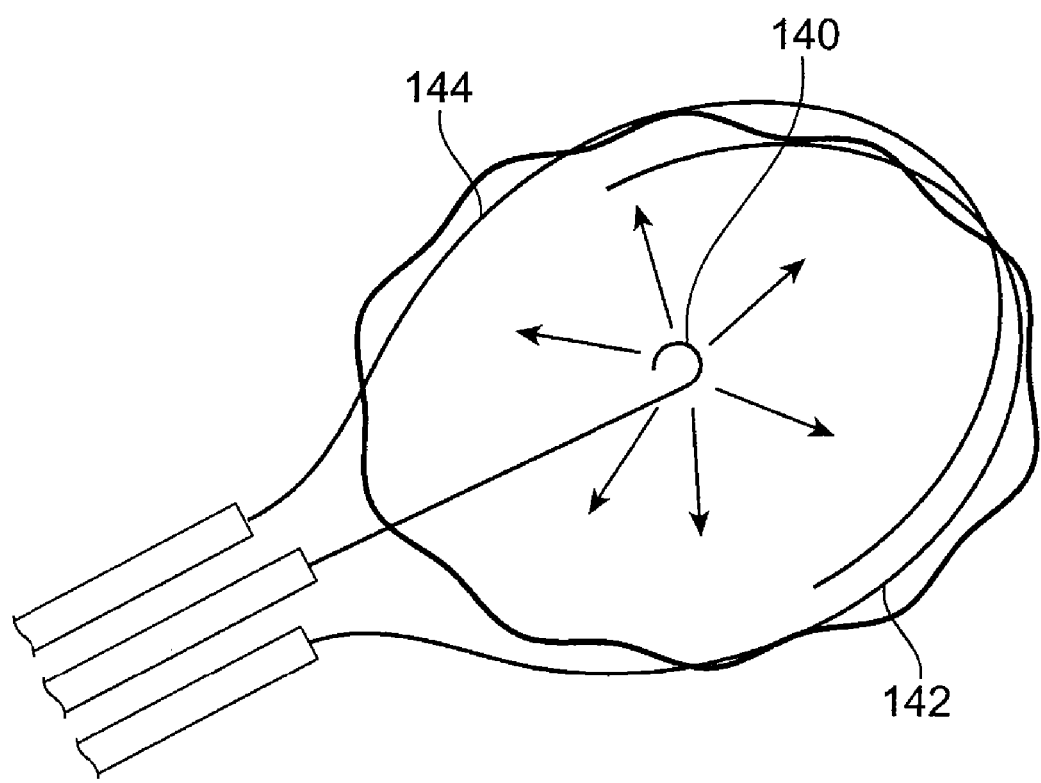
FIG. 10 shows a device according to an embodiment of the present invention.

Another embodiment of a device of the present invention is illustrated in FIG. 10. As discussed above, device configuration and electrode arrangement can be selected such that the electrical field radiates outwardly from about the center of the target tissue region and the electric field is substantially aligned with the division axes of certain cells of the growing tumor. More optimal application of electrical energy and alignment of the electric field with division axes of the growing tumor can be accomplished by both positioning of the electrodes in the target region and selected electrode configuration and/or geometry of the device. In one embodiment, for example, device can include an inner electrode 140 and a plurality of outer electrodes 142, 144 that are curved. The inner electrode 140 can additionally include a curved or nonlinear distal portion. Having curvature on electrodes can help select an applied electric field that radiates in a plurality of directions, including directions other than orthogonal to the longitudinal axis of the device or inner electrode. The outer curved electrodes substantially define the ablation volume and the inner electrode is positioned within the ablation volume. Arrows illustrate the field emanating from the center in a plurality of directions and substantially in line with dividing cancerous cells of the target tissue region. In some instances, the electric field provided by this configuration may align with a greater portion of cancerous cells of the target tissue region compared, for example, to the straight needle electrode configuration illustrated in FIGS. 9A through 9D.

As the ablation process is initiated, the field intensity is highest at the inner or central electrode and within tissue around and in close proximity to the inner or central electrode. As the ablation process progresses, cancerous cells near the inner electrode are observed to be destroyed or ablated first. The ablated cells effectively "liquefy" or assume properties of a low impedance, liquid-like material. The term "liquefy" is used herein for convenience and illustrative purposes, and does not necessarily imply any particular mechanism of ablation or cell death, which may include cell blebbing, apoptosis, lysis, or some other cellular process, and/or some combination thereof. Another possible cause of cell destruction may include disruption of cellular membrane integrity, e.g., including dielectric breakdown of one or more cellular membranes (see, e.g., below). The liquid-like material surrounds the central electrode and effectively enlarges the higher field intensity ablative area, with the highest field intensity ablative area being at the outer perimeter of the liquid-like material. Thus, the liquid-like material is said to become a "virtual electrode". As the ablation process progresses, the outer perimeter of the liquid-like material or "virtual electrode" expands, essentially ablating the target tissue region from the inside out. In some embodiments, target tissue regions were observed to be more pliable and soft or mushy following the ablation process. The ablated, liquid-like tumor tissue was eventually removed from the treatment site and/or absorbed by the surrounding tissue, and no longer detectible.

Figure 11A:
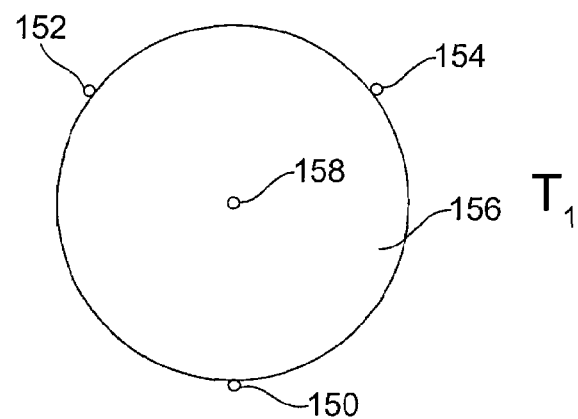
FIGS. 11A through 11C illustrates an ablation method according to an embodiment of the present invention.
Figure 11B:
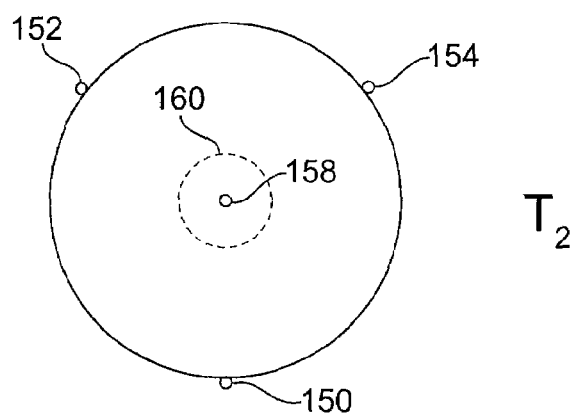
Figure 11C:
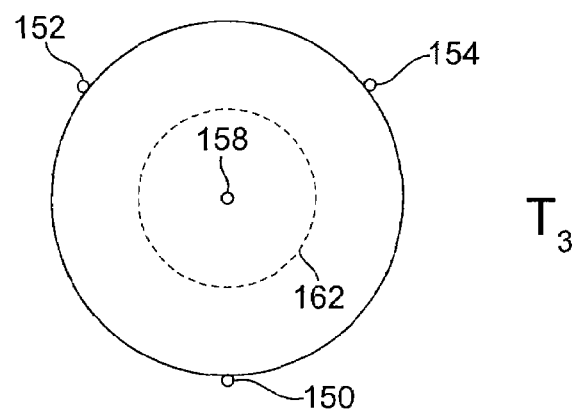

The virtual electrode effect is illustrated with reference to FIGS. 11A through 11C, showing a cross section view of electrodes positioned in a target tissue region. Outer electrodes 150, 152, 154 are positioned at about the margin or outer periphery of the tumor 156, and inner electrode 158 is positioned at about a center point of the volume defined by the outer electrodes 150, 152, 154. Ablation is shown at T1, or the beginning of the ablation process (FIG. 11A); T2 after ablation has begun with the expanding liquid-like tissue region 160 (FIG. 11B); and subsequent time T3, with the liquid-like tissue region 162 expanded further outward from the inner electrode 158 and toward the outer electrodes 150, 152, 154 (FIG. 11C).

The ablation process, including the progress thereof, can be monitored by detecting the associated change in impedance in the ablated tissue. Once the outer perimeter of the ablated, liquid-like tissue reaches the outer electrodes defining the ablation volume, the impedance stabilizes or levels out. Thus, the progress of the ablation process can be monitored by measuring change in impedance, and electric field application discontinued once a change in impedance is no longer observed.

Feedback measurements can also be used to ensure that the ablation of the target cancerous cells occurs by non-thermal ablation. In certain embodiments it may be desirable to generate as much field intensity at the inner electrode as possible without causing a hyper-thermal effect or thermal ablation.

Certain hyper-thermal effects would be observable and distinguishable from the desired non-thermal ablation of the present invention, since thermal ablation would cause destruction of the surrounding cells without the "liquefying" effect described above. For example, if cell destruction is caused by a thermal ablation process, the impedance of the treated tissue may not decrease since the impedance of cells that are charred or become necrotic due to thermal effects typically increases. In one embodiment, non-thermal ablation according to the present invention can include placement of a sensor, such as a thermocouple, within the target tissue region (e.g., proximate to the inner electrode), and selection of an applied field intensity as below the intensity that would cause thermal effects on the target cells.

Figure 12A:
FIGS. 12A through 12F illustrate exemplary electrodes according to various embodiments of the present invention.
Figure 12B:
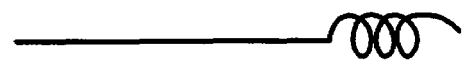
Figure 12C:
Figure 12D:
Figure 12E:
Figure 12F:

As stated above, in some instances, it may be desirable to increase the field intensity emanating from the position of the inner electrode within the target tissue region. In one embodiment of the present invention, field intensity can be increased by increasing the surface area of the inner electrode that is placed within the target tissue region. Various embodiments of increased surface area electrodes are illustrated in FIGS. 12A through 12F, though other configurations will be available. In one embodiment, the electrode includes a coiled distal portion that can further form a circular pattern (FIG. 12A), a corkscrew (FIG. 12B), or a simple coil (FIG. 12C). In another embodiment, a small wire mesh could be included at the electrode distal end, and expanded when placed within a target tissue region (FIG. 12D). In other embodiment, an electrode can include a "Litz" wire-type of electrode, where the distal end includes a plurality of small wires expanded in an array (FIG. 12E). In another embodiment, the distal portion can include a shape resembling two cones stacked base to base, or from a side view having a diamond shape (FIG. 12F). The pointed opposing distal and proximal portions of the double cone/diamond end can facilitate insertion and retraction of the electrode in tissue. Numerous other configurations are available and can include, for example, a ring, sphere, corkscrew, helix, concentric helixes, or plurality thereof, array of needles, length of non-resilient, string-like wire that is pushed out a tube and forms a small ball of wire similar to a string piling up randomly in a small container, and the like.

Figure 13A:
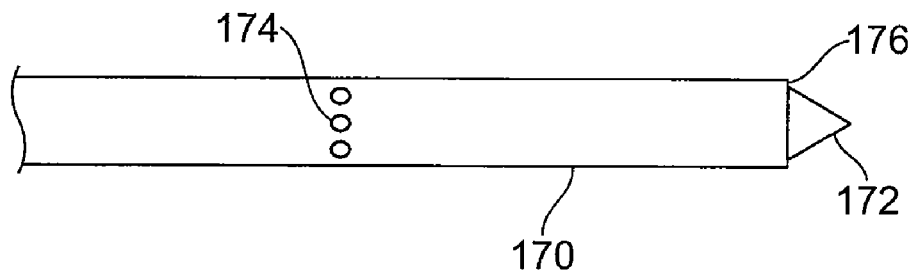
FIGS. 13A and 13B illustrate a device according to an embodiment of the present invention.
Figure 13B:
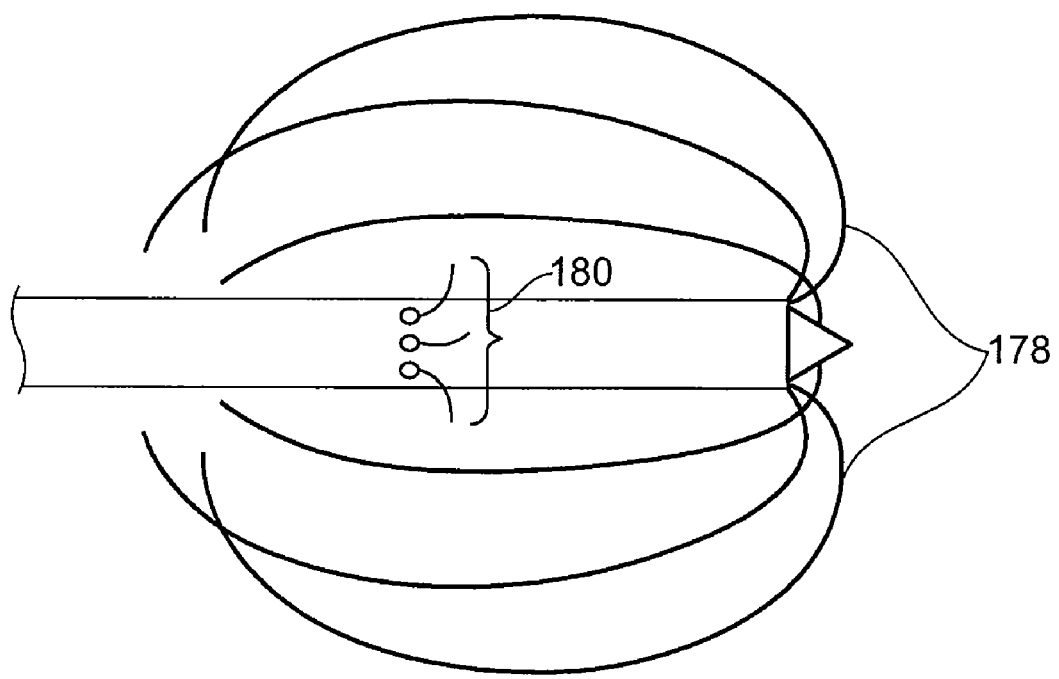

Another embodiment of a device of the present invention is shown in FIG. 13. The device includes a delivery member 170 with a tissue piercing distal portion 172. The delivery member includes a lumen and openings 174 on the body and at 176 the distal end. A plurality of electrodes are positionable within the lumen of the member. In a deployed state, outer electrodes 178 extend out the openings 176 at the distal end of the member 170 and invert in an umbrella-like orientation. The deployed outer electrodes 178 substantially define an ablation volume. Electrodes 180 extending out the openings 174 of the body are spaced from the outer electrodes 178 and positioned within the ablation volume.

Figure 14A:
FIGS. 14A and 14B illustrate a device according to another embodiment of the present invention.
Figure 14B:
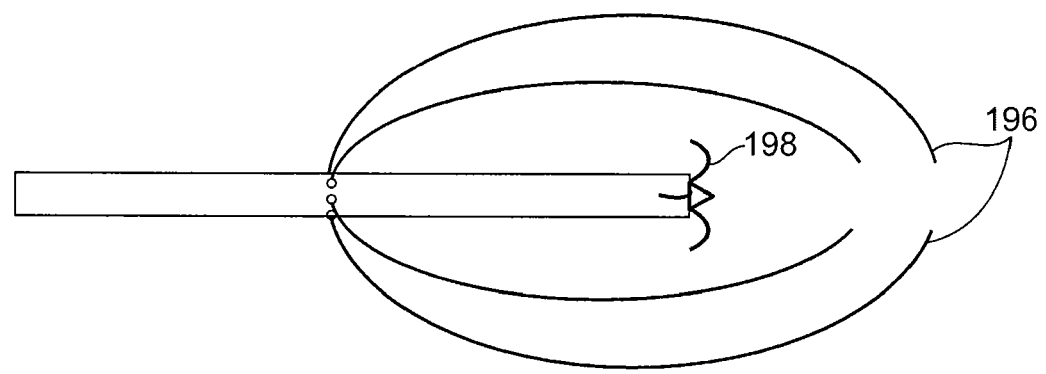

FIG. 14 illustrates a device similar to that shown in FIG. 13. Referring to FIG. 14, the device includes a delivery member 190 with a distal portion, openings 192 on the body and at the distal end 194. Outer electrodes 196 deploy distally out the body openings 192 and define a volume surrounding the electrodes 198 deployed and extending out the distal end opening 194.

Figure 15A:
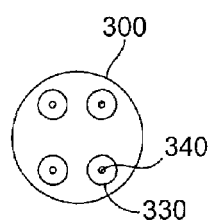
FIGS. 15A through 15D illustrates a device and ablation method according to an embodiment of the present invention.
Figure 15B:
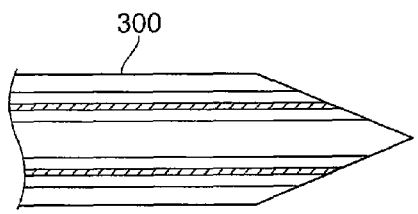
Figure 15C:
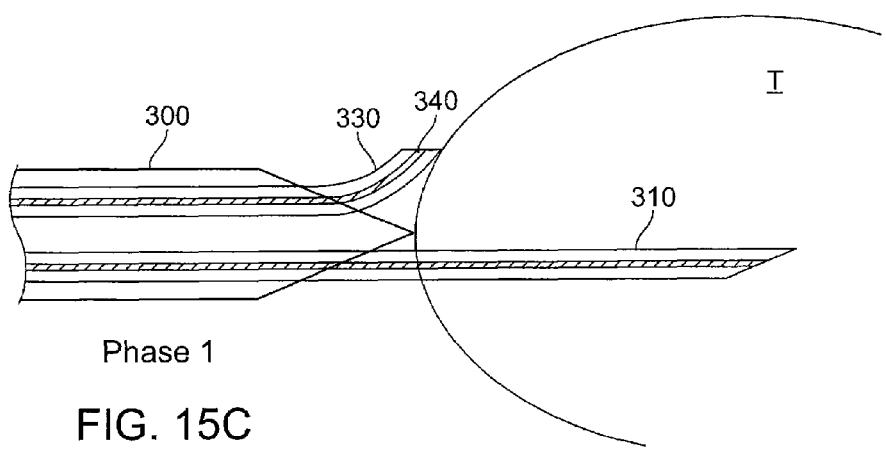
Figure 15D:
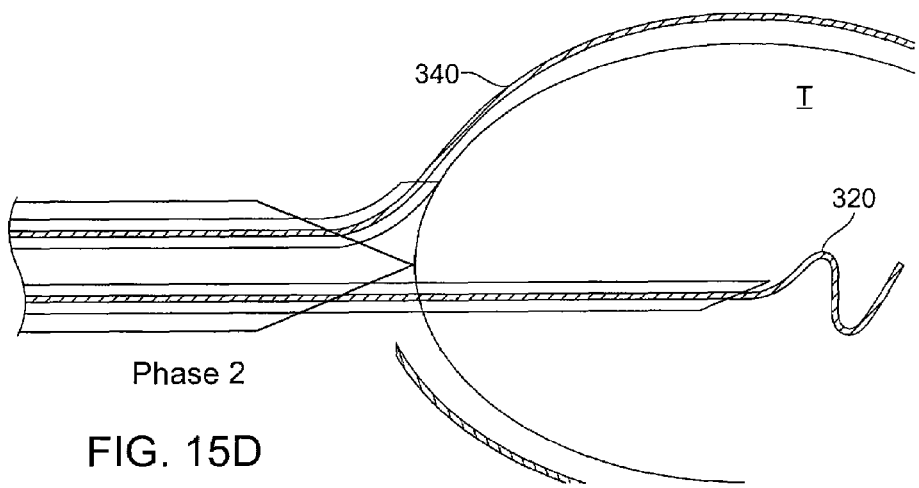

Another embodiment of a device of the invention is described with reference to FIGS. 15A through 15D. The device includes a plurality of electrodes positioned in a lumen of a delivery member 300 of a probe or delivery catheter, with each electrode positioned within a microcatheter as illustrated by microcatheter 330 and electrode 340, and each microcatheter positioned within the lumen of a delivery member 300. Microcatheters can act as guide tubes as advanced or deployed from delivery member 300 for initial aiming and/or positioning of electrodes contained therein (see below). FIG. 15A shows a cross-sectional front view of microcatheters positioned in the lumen of delivery member 300. The delivery member or probe 300 can include a tissue piercing end that is pointed or sharpened so as to more easily be inserted into the tissue of a patient, as illustrated in FIG. 15B. Similarly, a microcatheter (e.g., microcatheters 310, 330) can include a pointed or sharpened tissue piercing end. In use, the delivery member 300 can be advanced through the tissue of a patient and the distal end positioned proximate to a target tissue region (e.g., tumor "T") and the microcatheters are deployed from the delivery member for positioning of electrodes in a desired arrangement. As shown in phase 1 deployment (FIG. 15C), microcatheter 310 is advanced distally from the distal end of the delivery member and into the target tissue region, where the electrode 320 of the microcatheter can be deployed. Microcatheters can include shape memory metal (e.g., Nitinol) such that microcatheters assume a desired and/or predetermined shape when deployed from the delivery member 300, as illustrated with microcatheter 330. Thus, microcatheter 330 can also be deployed from the delivery member 300 to aim the electrode 340. In phase 2 deployment (FIG. 15D), electrode 340 is deployed in the direction aimed by microcatheter 330, such as around the outer perimeter of the target tissue region (e.g., tumor margin). Both microcatheters and electrodes positionable therein can be made of memory shape metal such as nitinol so as to assume a predetermined configuration when deployed. Other phases of use can further be included.

Figure 16:
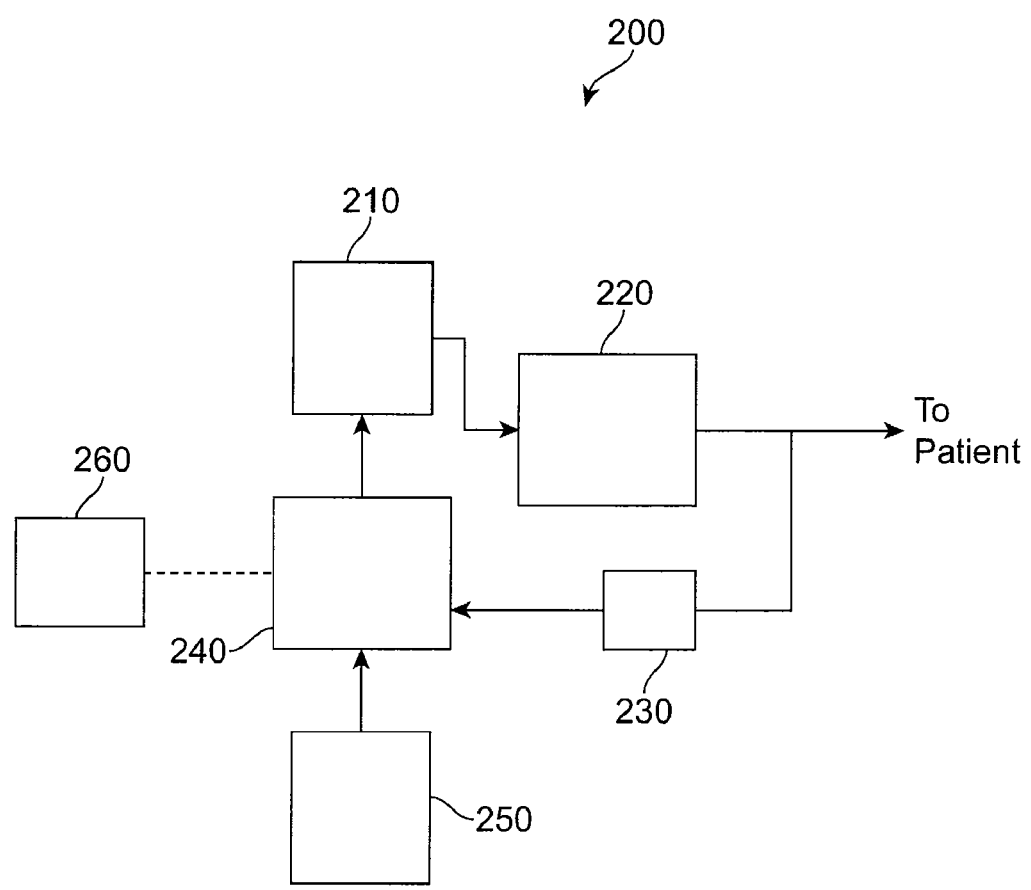
FIG. 16 illustrates a system according to an embodiment of the present invention.

A system according to an embodiment of the present invention is described with reference to FIG. 16. The system 200 can include incorporated therewith any device of the present invention for delivery of energy to the patient, and includes a power unit 210 that delivers energy to a driver unit 220 and then to electrode(s) of an inventive device. The components of the system individually or collectively, or in a combination of components, can comprise an energy source for a system of the invention. A power unit 210 can include any means of generating electrical power used for operating a device of the invention and applying electrical current to a target tissue as described herein. A power unit 210 can include, for example, one or more electrical generators, batteries (e.g., portable battery unit), and the like. One advantage of the systems of the present invention is the low power required for the ablation process. Thus, in one embodiment, a system of the invention can include a portable and/or battery operated device. A feedback unit 230 measures electric field delivery parameters and/or characteristics of the tissue of the target tissue region, measured parameters/characteristics including without limitation current, voltage, impedance, temperature, pH and the like. One or more sensors (e.g., temperature sensor, impedance sensor, thermocouple, etc.) can be included in the system and can be coupled with the device or system and/or separately positioned at or within the patient's tissue. These sensors and/or the feedback unit 230 can be used to monitor or control the delivery of energy to the tissue. The power unit 210 and/or other components of the system can be driven by a control unit 240, which may be coupled with a user interface 250 for input and/or control, for example, from a technician or physician. The control unit 240 and system 200 can be coupled with an imaging system 260 (see above) for locating and/or characterizing the target tissue region and/or location or positioning the device during use.

A control unit can include a, e.g., a computer or a wide variety of proprietary or commercially available computers or systems having one or more processing structures, a personal computer, and the like, with such systems often comprising data processing hardware and/or software configured to implement any one (or combination of) the method steps described herein. Any software will typically include machine readable code of programming instructions embodied in a tangible media such as a memory, a digital or optical recovering media, optical, electrical, or wireless telemetry signals, or the like, and one or more of these structures may also be used to transmit data and information between components of the system in any wide variety of distributed or centralized signal processing architectures.

Components of the system, including the controller, can be used to control the amount of power or electrical energy delivered to the target tissue. Energy may be delivered in a programmed or pre-determined amount or may begin as an initial setting with modifications to the electric field being made during the energy delivery and ablation process. In one embodiment, for example, the system can deliver energy in a "scanning mode", where electric field parameters, such as applied voltage and frequency, include delivery across a predetermined range. Feedback mechanisms can be used to monitor the electric field delivery in scanning mode and select from the delivery range parameters optimal for ablation of the tissue being targeted.

Methods and techniques of the present invention may employ a single device or a plurality of devices. In one embodiment, for example, a device of the present invention (e.g., device as illustrated in FIGS. 2A through 2C) can be positioned within a target tissue region as described above. A second device can then be positioned within the target tissue region or in another target tissue region, either of part of the same tumor or at a separate tumor. In one embodiment, for example, a first device is positioned in a target tissue region, and a second device can be positioned in the target tissue region, where the second device is positioned at an angle (e.g., 90 degree angle) relative the first device. Additionally, the same device may be positioned in a different orientation and/or location at a separate time point.

Systems and devices of the present invention can, though not necessarily, be used in conjunction with other systems, ablation systems, cancer treatment systems, such as drug delivery, local or systemic delivery, radiology or nuclear medicine systems, and the like. Similarly, devices can be modified to incorporate components and/or aspects of other systems, such as drug delivery systems, including drug delivery needles, electrodes, etc.

Figure 17A:
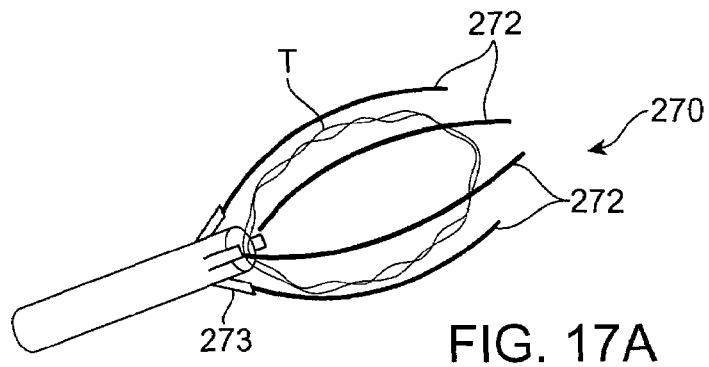
FIG. 17A through 17D illustrates a system according to an embodiment of the present invention.
Figure 17B:
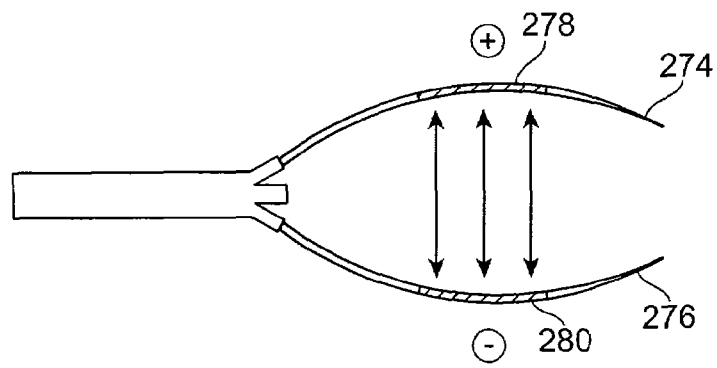
Figure 17C:
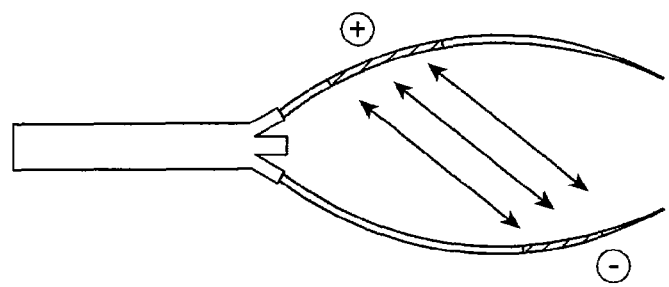
Figure 17D:
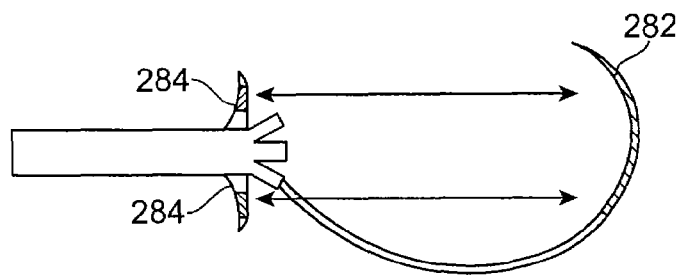

While some embodiments of the present invention can include positioning of an electrode directly within the target tissue region, in some instances it may be desirable to apply an electric field as described above, through the target tissue region (e.g., radially), in the absence of an electrode positioned within the defined ablation volume. Referring to FIGS. 17A through 17D, an ablation probe/device of the present invention according to another embodiment of the present invention is described. The device 270, as illustrated in FIG. 17A, is configured for delivery of an electric field to a target tissue region ("T") such that the electric filed is applied radially through target tissue region and in a plurality of different directions. The device include a plurality of electrodes 272 that can be positioned to substantially define an ablation volume or target region. In some embodiments, electrodes can be deployable from a catheter-type device (e.g., similar to as configurations described above), e.g., from a distal portion, that can be advanced to the a target region. Similar to embodiments described above, the device 270 can include a delivery member having a lumen with microcatheters positioned within the lumen of a delivery member, and electrodes 272 each disposed in a microcatheter. As illustrated, microcatheter 273 can be deployed from the delivery member and may act as an initial advancement or guide tube as advanced or deployed from delivery member for initial aiming and/or positioning of electrode disposed therein. In use, treatment can include activation of electrodes 272 (e.g., opposing electrodes) in pairs, such that the electrode pairs define a circuit and an applied field extends between the two electrodes of the pair. Different electrode pairs can be activated to apply electric fields to different portions of the target tissue and/or fields having different directions/orientations. Electrodes can be configured to have defined electrically active areas, for example, by including insulated and non-insulated portions. FIG. 17B illustrates activation of opposing electrode pairs 274, 276 of a device that can include a plurality of electrode pairs, and field generation between the activated electrode pairs as illustrated by the arrows. Electrodes 274, 276 can each include active portions 278, 280, respectively. Electrodes can each include a single or continuous active area, as shown, or a plurality of active areas along a length of an electrode (not shown). Active areas can be positioned at various locations on electrodes so as to select the direction/orientation of the field applied by a given pair (see, e.g., FIG. 17C). FIG. 17D illustrates an embodiment of an electrode pair 282, 284 having an electrode configuration for generating a field that runs approximately parallel to the longitudinal axis of the probe. A device can include a plurality of electrode pairs configured as described, with different pairs of the plurality applying fields in different directions across the target tissue. Configuration and arrangement of electrodes in this manner can permit application of current field radially through the tumor and in a plurality of different directions, with fields running through an approximate center point of the ablation volume or target tissue. Electrode pairs can be activated individually or sequentially such that only one electrode pair is activated at any one moment, or multiple pairs can be activated simultaneously.

While embodiments of the present invention are discussed in terms of use for non-thermal ablation and destruction of cancerous cells as described above, in some instances systems and probes can be configured for delivering energy sufficient for other types of tissue ablation, such as thermal RF ablation, microwave ablation, irreversible electroporation via high-voltage direct current, and the like. For example, a system of the invention can include a power unit configured for delivery of energy suitable for any one or more types of tissue ablations. In fact, certain probe configurations have designs (e.g., electrode arrangements) that can provide improved delivery of a various types of tissue ablation, including, e.g., improved delivery of thermal RF ablation, and the like. And treatment according to methods of the present invention can include delivery of one or more types of tissue ablations for a given treatment. In some instances, for example, treatment may include one or more ablation delivery modes, such as one mode where non-thermal tissue ablation is delivered, which can precede or follow another ablation mode, such as thermal RF tissue ablation. For example, in one embodiment, treatment can include delivery of non-thermal tissue ablation followed by a shorter application or pulse of energy to produce a thermal mediated effect, e.g., to help "sterilize" one or more components of the probe for withdrawal from the target tissue through the entry track and reduced risk of tracking any potentially viable cancer cells through tissue during probe withdrawal.

In some embodiments, systems of the present invention can further include certain components and aspects for positioning and/or stabilizing probes and other components during the energy delivery process. For example, in instances where a phase of treatment, such as energy application, is expected to exceed more than a few minutes, it may be desirable to include a positioning or stabilizing structure to maintain a probe in a desired position/location without specifically requiring a user (e.g., surgeon) to hand-hold the probe. Thus a system can include a harness, belt, clamp, or other structure to maintain probe positioning. Systems can be designed for ambulatory use so as to allow for movement of the patient (e.g., shifting, walking, etc.) during treatment. In fact, the low-power requirements and corresponding design options (e.g., battery powered system) may make the current systems particularly well suited for use as an ambulatory system.

In some instances, it may be desirable to remove ablated tissue from the target tissue region at a stage of the ablation process described herein. For example, it has been observed that, in some instances, removal of ablated tissue can improve treatment and/or recovery of the subject, and possibly reduce stress and/or toxicity (e.g., local tissue toxicity, systemic toxicity, etc.) associated with the ablation process of the present invention.

Various devices and methodologies can be utilized for removing the ablated tissue. In some instances, as described above, the ablated tissue can effectively "liquefy" or assume properties of a liquid-like material. The liquid ablated tissue can then be drained or removed from the target tissue region. In one embodiment, removal of the ablated tissue can be as simple as allowing ablated tissue to leak or ooze out of target tissue region (e.g., with or without application of a force or pressure to the target tissue region or tissue proximate thereto), for example, by leaking out holes or piercings in the tissue, including, e.g., entry holes through which the device/electrodes are introduced into the target tissue region. In other embodiments, removal of ablated tissue can be more deliberate or controlled. The removal can be accomplished using a device or apparatus separate from the ablation device, such as a syringe or other liquid removing device, or the removal can be accomplished using the ablation device further configured for the tissue removal. A device configured for removal of ablated tissue can include a tissue removal member, which can be deployable from a delivery catheter. In one embodiment, the removal member includes a catheter-like member having a lumen for carrying liquid. The removal member can be separate from or combined with other components of the device, such as an electrode (e.g., central electrode), delivery member, and the like. Various configurations of removal members capable of removing ablated tissue from the target tissue region will be envisioned and certain exemplary embodiments are described herein. It will also be recognized that while removal members are discussed with respect to use in removing ablated tissue from the target tissue region, in some instances, removal members may have additional or multipurpose functionality and, for example, may be additionally used to deliver an agent or material (e.g., drug, chemotherapeutic agent, flushing buffer, etc.) to the target tissue region.

Figure 18:
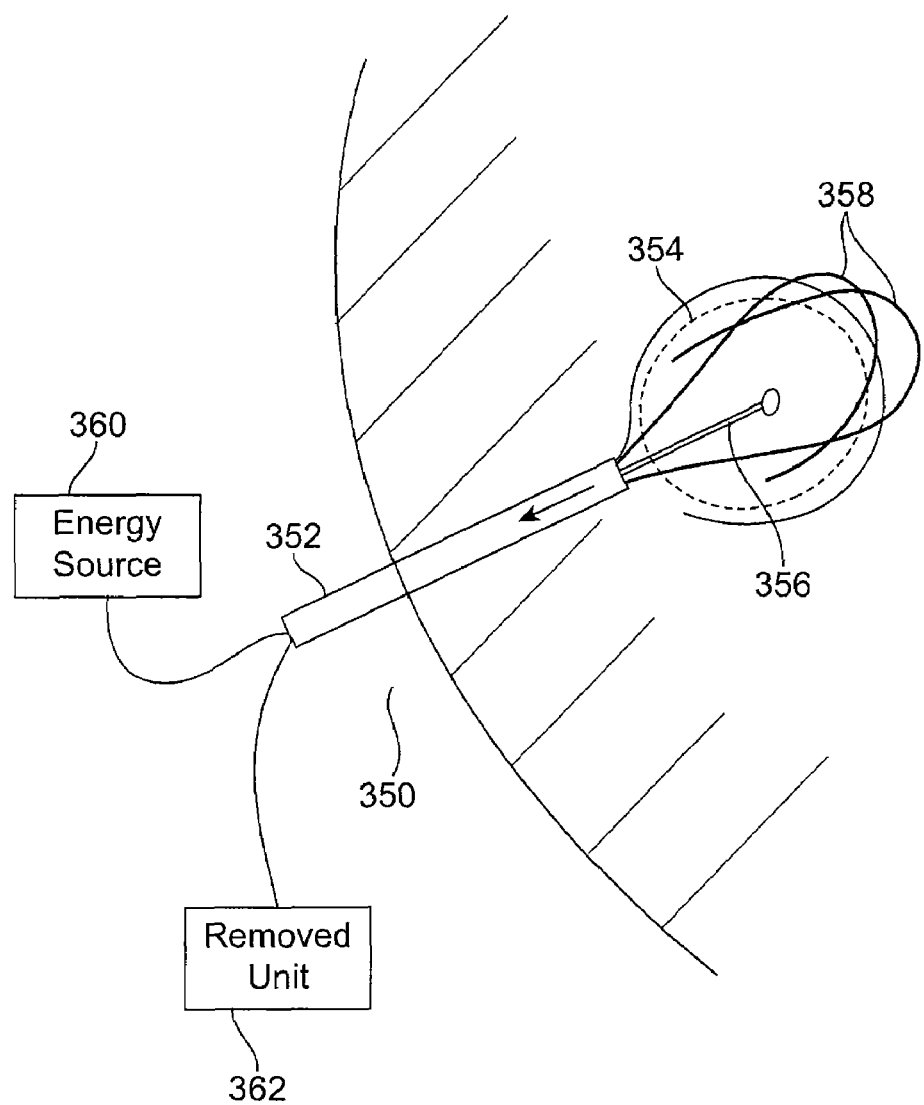
FIG. 18 illustrates a device according to an embodiment of the present invention, where the device is configured for removing ablated tissue from a target tissue region.

Referring to FIG. 18, a device of the present invention is described according to another embodiment of the present invention, where the device is configured for removing ablated tissue from the target tissue region. The device 350 includes a delivery member 352 a distal portion of which can be positioned within or proximate to a target tissue region 354 (e.g., tumor) and a removal member 356 and outer electrodes 358 deployed from a distal portion of the delivery member 352 and positioned at the target tissue region 354 as previously described above. The removal member 356 or portion thereof (e.g., distal portion) can also serve as a central electrode. The device 350 can be coupled to an energy source 360, which provides an electric current to ablate cancerous cells of the target tissue region 354, e.g., as described above. A removal unit 362 can be coupled to the device 350 to provide removal of ablated tissue from the target tissue region 354. The removal unit 362 will include component(s) that provide for removal of the ablated tissue, and will typically be configured to provide a removal force, such as pressure or suction, and/or collection apparatus to aid in ablated tissue removal or collection. In one embodiment, the removal member 356 can include a catheter-like member having a lumen with holes or ports positioned on a portion of the removal member 356 so as to allow collection and removal of ablated tissue from the target tissue region 354. As the removal member 356 is coupled with the removal unit 362, a force or suction can be applied to the target tissue region 354, e.g., during and/or subsequent to energy delivery, as to collect/remove ablated tissue from the target tissue region 354.

Figure 19A:
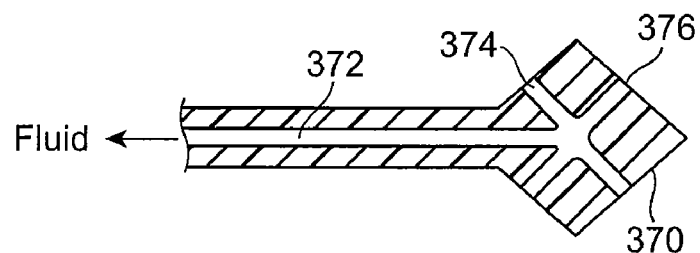
FIGS. 19A and 19B illustrate removal members of a device according to exemplary embodiments of the present invention.
Figure 19B:
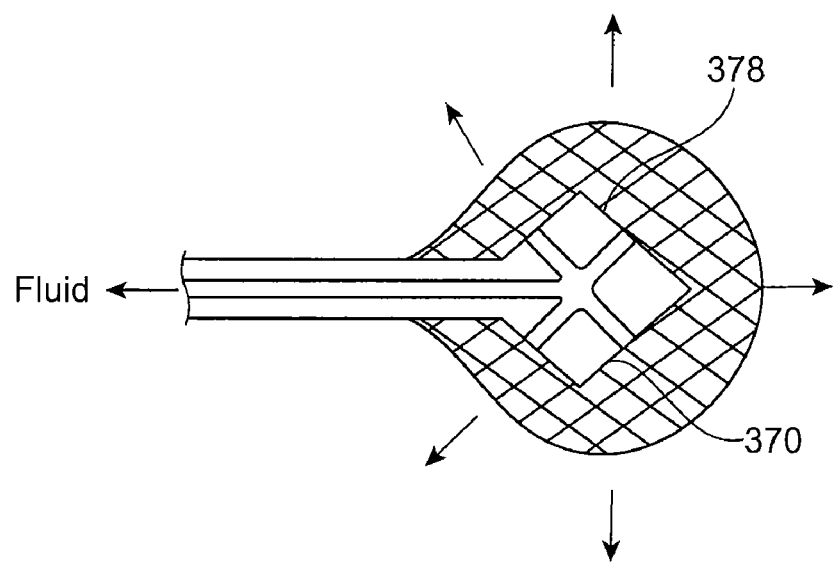

As described above, various configurations and embodiments of a removal member are envisioned according to the present invention. Removal members according to exemplary embodiments of the invention are described with reference to FIGS. 19A and 19B. A removal member 370, for example, can include a lumen 372 fluidically connected to openings 374 at a portion of the device, such as a distal portion 376. The distal portion can also be configured to serve as an electrode (e.g., central electrode). In use, ablated tissue or fluid can enter the openings 374 and pass through the lumen 372 for removal from a tissue region. In another embodiment, a removal member can further include an expandable mesh 378. The mesh 378 can include an electrically conductive material and/or shape memory material (e.g., Nitinol™) and can further serve as an electrode of the device. In use, the mesh 378 can be expanded outwardly (e.g., as illustrated by arrows in FIG. 19B) at a stage of the ablation process (e.g., during energy delivery) and can provide an outward force or pressure. As target tissue "liquefies" during the ablation process, the outward pressure from the expanding mesh 378 can allow liquid/ablated tissue to flow through openings of the delivery member 370 and through the lumen, e.g., either passively or under an applied negative pressure or suction. Where the mesh 378 also serves as an electrode, the expanding mesh 378 allows the electrode (e.g., center electrode) to expand during the ablation process.

Figure 20:
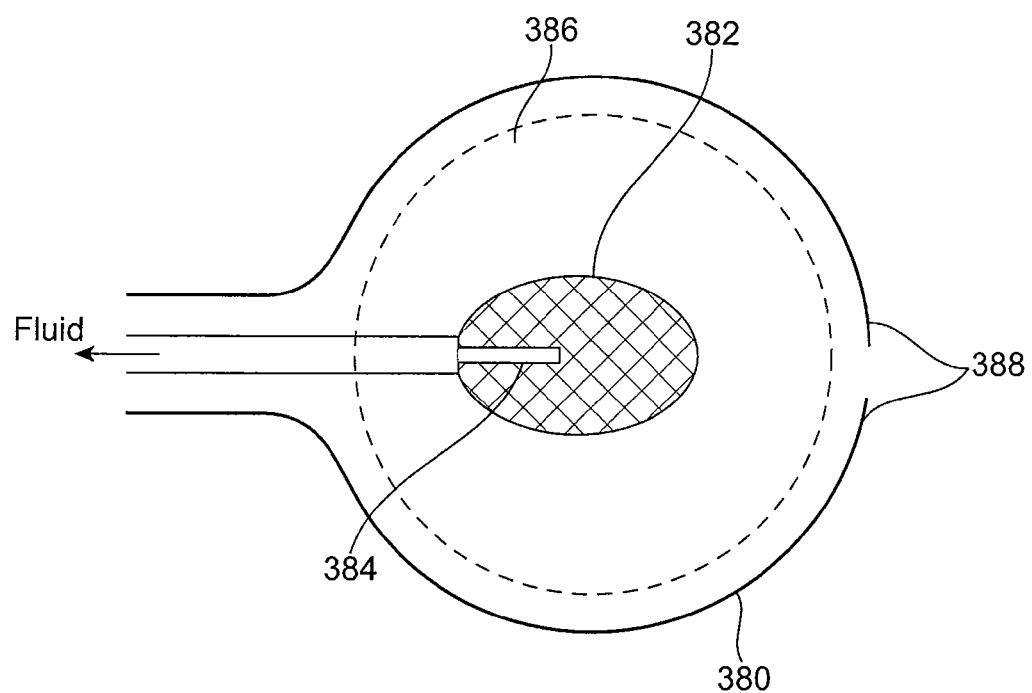
FIG. 20 shows a device configured for removing ablated tissue from a target tissue region, according to another embodiment of the present invention.

Another embodiment of a device of the invention is described with reference to FIG. 20. Similar to the device illustrated in FIG. 19B, the device 380 includes a mesh 382 defining a volume and a removal member 384 positioned within the volume. The mesh 382 can be positioned within a target tissue region 386 and can serve as an electrode (e.g., center electrode). The device further includes outer electrodes 388. The removal member 384 is illustrated as a tube-like catheter and can include a distal end opening. The mesh 382 can be used for energy delivery and may additionally serve as a screen or filter that allows passage of more fluid-like material and smaller particles (e.g., cells, cellular debris, etc.) to reach the removal member 384, while preventing larger particles and tissue from clogging the removal member 384.

Figure 21:
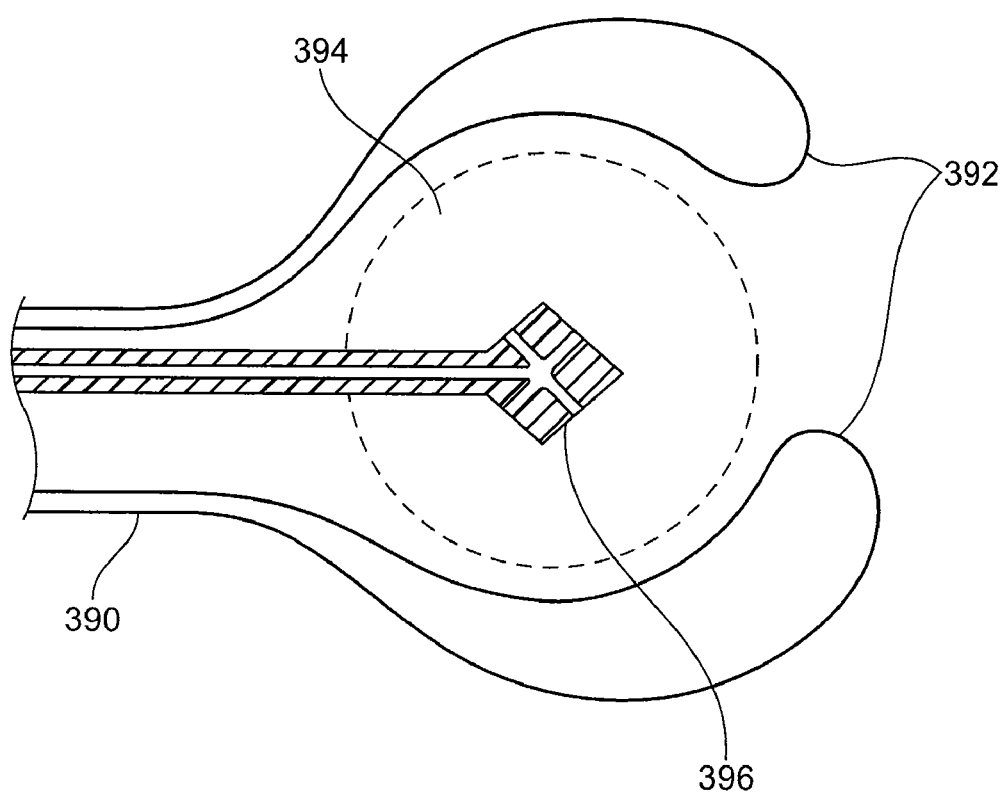
FIG. 21 illustrates device having expandable members and configured for removing ablated tissue from a target tissue region, according to another embodiment of the present invention.

In another embodiment of the present invention, removal of liquid and/or ablated tissue can include application of a pressure or force at or proximate to the target tissue region. As illustrated in FIG. 21, a device 390 can include expandable members 392, such as balloons, that can be placed at or proximate to the outer periphery of a target tissue region 394, with a removal member 396 that can be positioned within the target tissue region 394. The removal member 396 can optionally be configured to serve as an electrode. Expandable members 392 can be expanded as to apply a force of pressure to the target tissue region 394 and allow liquid, such as liquid ablated tissue, to flow through the removal member 396. Expandable members 392 can optionally be at least partially coated with or configured to include a conductive material so that the expandable members can serve as electrodes (e.g., outer electrodes).

Figure 22:
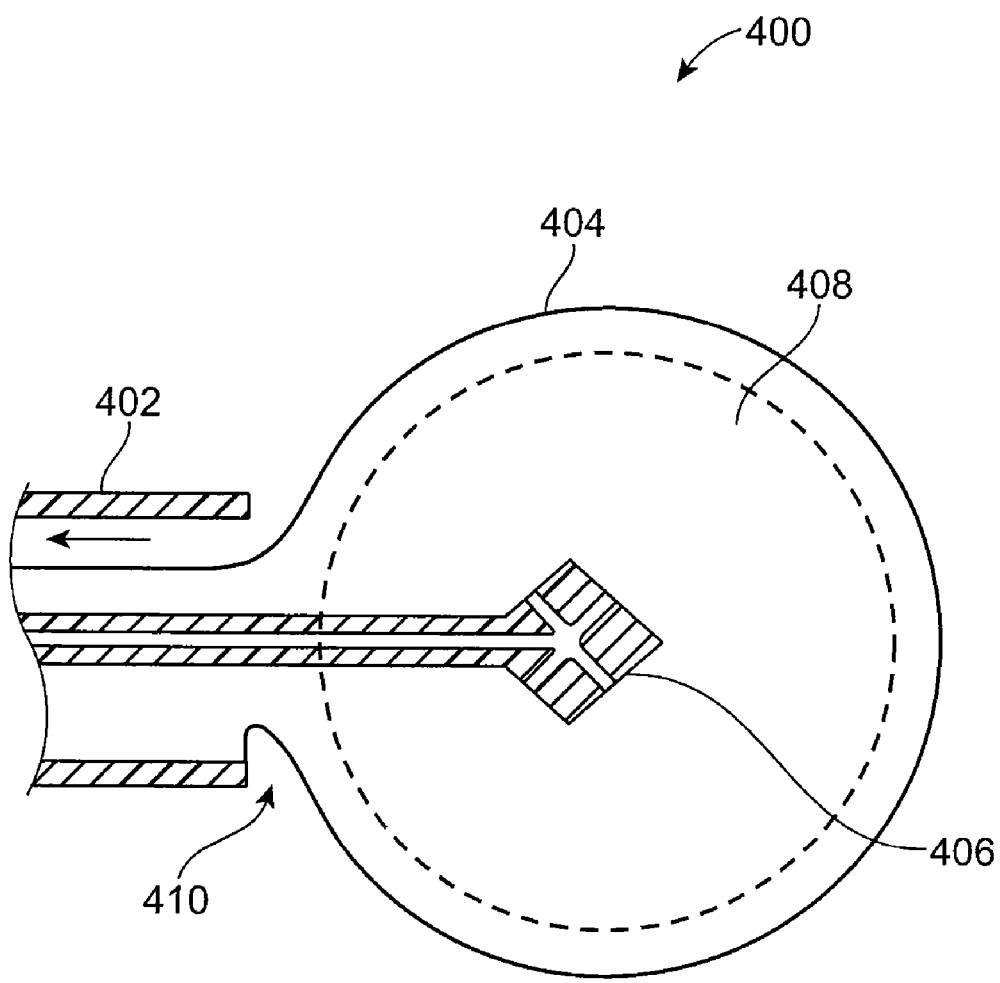
FIG. 22 illustrates another device according to another embodiment of the present invention, the device configured for removing ablated tissue from a target tissue region.

Referring to FIG. 22, another embodiment of a device of the present invention is described, where the device is configured for removing ablated tissue from the target tissue region. The device 400 includes a delivery member 402, an outer electrode 404, and a removal member 406. The removal member 406 is positioned within a target tissue region 408. The outer electrode 404 can be deployed to at least partially encircle the target tissue region 408 and the outer electrode 404 configured such that the distal portion of the electrode 404 is attachable to a portion of the device, such as a portion 410 of the delivery member 402. In this way, the outer electrode 404 forms a sort of "lasso" around the target tissue region 408. A force or tension can be applied to a proximal portion of the outer electrode 404 such that the volume defined by the outer electrode 404 decreases or contracts and applies a pressure to the target tissue region 408. The applied pressure can "squeeze" the target tissue region 408, thereby allowing fluid/ablated tissue to more easily pass through the removal member 406 and be removed from the target tissue region 408.

The following examples are intended to illustrate but not limit the invention.

EXAMPLES

One series of testing included treatment of breast cancer tumor models. In one example, testing was done on Female Fisher-344 rats (Charles River), with body weight 230-250 grams. Rat breast cancer cells (MTLn-3) were initially grown in culture and subcutaneous tumors were produced by implanting cells from cultures into the abdomen of the animal. When the tumors grew to approximately 1 cm or greater in diameter, the ablation treatment was administered. 18 solid breast tumors in rats were treated.

Ablation treatment included insertion of an ablation probe including a stainless steel needle electrode array percutaneously, through the skin and directly into the tumor, and then applying tumor treating electric fields. The needle array included a central needle surrounded with three parallel outer needles of approximate equal spacing. Probe design, including needle length and arrangement, were selected to traverse the approximate diameter of tumors being treated and needles were about 1 cm in length. The outer needles were spaced about 0.5 cm from the central needle. The central needle was activated with the tumor treating voltage, and the surrounding needles provided the return path for the current. No earth ground was provided (e.g., electrically "floating" system) where probes were operated in "bi-polar mode" as described, and the device included a battery powered source.

Using the above described probe and configuration of needles, the treating field was contained within a cylinder approximately 1 cm in diameter and 1 cm long, the volume of which was substantially occupied the tumor. The applied AC voltage was about 10-12 volts peak, at about 20-30 mA (starting current). The frequency was about 98 Khz.

A feedback circuit was included to measure the total current into the tumor during treatment. One hypothesis from preliminary experimentation was that when tumors cells began destruction from the applied field (e.g., lyse, disintegrate, spill cytoplasm, etc.), the current would actually increase due, for example, to increased conductance within the tumor area due to contents of the destroyed cells (e.g., cytoplasm, etc.) being more conductive than cells substantially in tact. Results indicated that the circuit worked as hypothesized. The current began to increase after the start of treatment in each case, indicating that treatment was effectively taking place. Observed current increase also provided indication of when the process reached a stage of substantial completion. For example, an observation of no further increase in current indicated that treatment could be discontinued. This plateau in current was observed to occur at approximately 40 mA, and typically within approximately 90 minutes into the treatment.

Tumors began to show cell destruction almost immediately after power was applied. Significant destruction occurred within 30 minutes into the treatment. In some instances, treatment was terminated after 30 minutes and the tumors were almost undetectable. In other treatment groups, treatment was completed at about 90 minutes, or within 3 hours. In all cases the treated tumor was virtually undetectable. Controls were included to confirm that tumor destruction was a result of the applied field. In one group, needles were inserted with no power applied as a control. Continued tumor growth was observed in controls.

A group of rats that were treated were selected for long term viability study and were not sacrificed following treatment. Survival was confirmed at one point at greater than 12 months from the date of treatment, which was >17 times the expected survival in the animal model when not having any treatment (e.g., about 3 weeks). These rats currently remain alive. Survival observations and histological analysis (e.g., see below) indicated destruction of a vast majority, if not substantially all, of the cancer cells within target tissue subject to treatment as described.

As noted above, treatment typically resulted in a sort of liquification of cancerous cells/tissue. Following treatment, a clear to pinkish fluid was observed present in the target tissue region subject to treatment, which could leak from needle entry locations and further excreted upon compression or application of pressure to the treated region. Histological analysis was performed on the fluid and the tumor area after treatment. The histology showed that the fluid primarily consisted of destroyed cancer cells, with destroyed cells appearing substantially necrotic and non-viable. Testing of pH indicated that the removed fluid was more highly alkaline (e.g., pH of about 7.8 or greater) than typical physiological fluids. Observed treatment areas were about 80-90% necrotic or non-viable cancer cells. The treated area which was not necrotic (e.g., typically about 10-20% of target tissue) appeared to be the part of the area which was healthy, non cancerous tissue. Thus, the results indicated a selective destruction of cancerous cells, while leaving healthy cells substantially unharmed or viable.

The observed treatment appeared to have no significant side effects. Surviving subjects not sacrificed for further analysis have exhibited no debilitation or any noticeable signs of negative side effects (viability, behavior, or otherwise) after treatment. No significant distress or discomfort, or irritation of the treatment region, due to application of energy was observed in the subjects. During treatment the rats appear comfortable, i.e., eating, drinking, and sleeping even though they are not anesthetized during treatment.

The only observation of a potential side effect appeared to be a result of non-removal of the fluid or ablated tissue following treatment. When fluid was not removed from the treatment region following treatment, subjects appeared lethargic for several hours and recovery time was increased compared to rats subject to fluid removal following ablation treatment.

As noted above, treatment as described was observed to be selective in destroying cancerous cells within a defined target tissue region. Without being bound by any particular theory, one or more reasons could explain the selective nature of the described treatment. One reason for the observed selectivity appeared to be design of the ablation probe—treatment was substantially confined to a treatment volume as defined by the positioning of the electrodes. Only the tissue is within the probe's outer electrodes appeared to receive the delivered energy and that is the area the electric field almost exclusively covers. The field does not appear to extend outside of the volume defined by the outer electrodes.

Second, selectivity may be inherent to the mechanism of cell destruction. The cell ablation is distinguished from a primarily thermal-mediated ablation as performed in known high-frequency RF thermal ablation, or microwave ablation techniques, nor is the effect due to high voltage irreversible electroporation by application high voltage direct current as has been previously described elsewhere. All of these previously taught methods, by design, destroy normal tissue as well as cancer. Techniques of the present invention make use of voltage, power and frequency ranges that are not within the range of thermal or high voltage ablation.

Furthermore, without being bound to any particular theory, additional cellular-level effects of the current techniques may cause selective destruction of cancerous cells compared to non-cancerous cells. The energy application as described herein appears to mediate breakdown of the cell membrane integrity. One potential reason for the breakdown of the cell membrane and/or destruction of cancer cells may include disruption of cell cycle progression and cell mitosis by the applied electric field, with the disruption triggering cell destruction (e.g., necrosis, apoptosis, disintegration) as has been observed herein. Since cancer cells in a tumor are actively dividing and proliferating and, therefore actively progressing through the cell cycle/mitosis at a much higher rate compared to orders of magnitude slower rates of non-cancerous or healthy cells, this energy application as described can be selective to cancer cells.

Another possible cause of cell destruction may include dielectric breakdown of the cellular membrane. Cell membranes are known to have a dielectric breakdown threshold, above which the cell is destroyed. A normal cell typically has a higher threshold than a cancer cell. Thus, it is possible to selectively breakdown a cancer cell membrane without harming a normal cell where the applied energy is above the dielectric breakdown threshold for cancerous cells but below that of normal/healthy cells. Breakdown in membrane integrity resulting from treatment as described herein may occur in both extracellular membranes as well as intracellular membranes, for example, causing rupture of lysosomes containing components (e.g., degradative enzymes, etc.) that further lead to cell destruction. Rupturing of cells and spilling of cellular contents can negatively effect nearby cells, resulting in a sort of cascade of cellular destruction. Treatment may also stimulate an immune response that can "clean up" the treatment region and may further destroy any residual/viable cancer cells not destroyed or removed. Other disruptions and/or mechanisms of action may also occur. Regardless of any particular mechanism of action, where cellular disruption occurs as described, the resulting fluid appears to further act in some instances as a sort of virtual electrode, making the electrode larger and larger in diameter, and finally substantially covering the entire target tissue region.

It is understood that the examples and embodiments described herein are for illustrative purposes only and that various modifications or changes in light thereof will be suggested to persons skilled in the art and are included within the spirit and purview of this application and scope of the appended claims. Numerous different combinations are possible, and such combinations are considered part of the present invention.

What is claimed is:

1. A method of destroying cancerous cells of a tissue, comprising:
    applying an alternating current to a target tissue region so as to non-thermally ablate cancerous cells within the target tissue while maintaining ablated tissue temperature elevations at less than about 10 degrees C., the applied current liquefying at least a portion of the target tissue; and removing liquified tissue from the target tissue region.

2. The method of claim 1, wherein the liquefied tissue comprises destroyed cancerous cells.

3. The method of claim 2, wherein the destroyed cancerous cells comprise apoptotic or necrotic cells.

4. The method of claim 2, wherein the destroyed cancerous cells comprise lysed or membrane ruptured cells.

5. The method of claim 1, wherein removal of the liquefied tissue reduces recovery time in a treated subject compared to non-removal of the liquefied tissue.

6. The method of claim 1, wherein removing liquefied tissue comprises applying pressure to the target tissue region.

7. The method of claim 1, wherein removing liquefied tissue comprises insertion of a removal member into the target tissue region.

8. The method of claim 1, wherein removing liquefied tissue occurs following application of the current.

9. The method of claim 1, wherein the applied current provides low-power, non-thermal tissue ablation.

10. The method of claim 1, wherein the electrical current provides a voltage field less than about 50 V/cm the current comprises a frequency between about 50 kHz and about 300 kHz.

11. The method of claim 1, wherein the applied current provides one or more electric fields extending radially through the target tissue region.

12. The method of claim 1, wherein the target tissue region comprises a tumor.

13. A method of delivering an electric field to a tissue and destroying cancerous cells, comprising:
    positioning a plurality of electrodes within a target tissue region comprising cancerous cells, the plurality comprising a first electrode and a plurality of secondary electrodes spaced from the first electrode;
    applying an alternating electrical current to the target tissue so as to establish current flow between the first electrode and secondary electrodes, and in a plurality of different directions through the target tissue, and selectively ablate cancerous cells of the target tissue region around the first electrode, the current comprising a frequency of less than about 300 kHz, and wherein the applied electrical current is selected such that elevation in target tissue temperature during current application is less than about 10 degrees C. above body temperature; and
    removing ablated tissue from the target tissue region.

14. The method of claim 13, wherein the ablated target tissue comprises a liquid.

15. The method of claim 14, wherein the liquid comprises destroyed cancerous cells.

16. The method of claim 13, wherein the electrical current provides a voltage field less about 50V/cm or less, and a frequency between about 50 kHz and about 300 kHz.

17. The method of claim 13, wherein the ablation is selective to cancerous cells.

18. The method of claim 13, wherein the applied voltage field is substantially aligned with division axes of dividing cancerous cells of the target tissue region.

19. The method of claim 13, wherein applying the electric field comprises disrupting mitosis or cell cycle progression of dividing cancerous cells.

20. The method of claim 13, wherein applying the electric field comprises disrupting cellular membrane integrity of cancerous cells.

21. The method of claim 13, wherein the electrode is disposed substantially at about the center of the target tissue region.

22. A method of delivering an electrical field to a tissue, comprising:
    advancing a probe comprising a plurality of electrodes to a target tissue region comprising cancerous cells, the plurality comprising a first electrode and a plurality of secondary electrodes spaced from the first electrode, and positioning the plurality of electrodes so as to at least partially define an ablation volume with the positioned secondary electrodes, with the first electrode disposed within the ablation volume;
    applying in a first mode an alternating current so as to establish current flow between the first electrode and secondary electrodes and provide electric fields extending radially through the volume or in a plurality of different directions, and selectively destroy cancerous-cells compared to non-cancerous cells within the volume while maintaining target tissue temperature elevations at less than about 10 degrees C., the current comprising a frequency of less than about 300 kHz;
    removing treated tissue from the target tissue region.

23. The method of claim 22, further comprising applying in a second mode a current to the target tissue so as to thermally ablate cells of the target tissue.

24. A method of delivering an electrical field to a tissue, comprising:
    advancing a probe comprising a plurality of electrodes to a target tissue region comprising cancerous cells, the plurality comprising a first electrode and a plurality secondary electrodes spaced from the first electrode, and positioning the plurality of electrodes so as to at least partially define an ablation volume with the positioned secondary electrodes, wherein the first electrode is disposed within the ablation volume;
    applying an alternating current in a first mode so as to establish current flow between the first electrode and one or more secondary electrodes, and in a plurality of different directions or extending radially through the volume, and selectively destroy cancerous cells compared to non-cancerous cells within the volume, the current-comprising a voltage field of less than about 50 V/cm and a frequency of between about 50 kHz and about 300 kHz;
    detecting a temperature of the target tissue region during current application; and
    modifying the applied electric current at least partially in response to a change in detected temperature such that target tissue temperature elevations during current application are maintained at about 2 degrees C. to about 10 degrees C. above normal body temperature during the first mode for cancer cell destruction.

25. The method of claim 24, wherein the current applied in the first mode stimulates an immune response to the target tissue.

26. The method of claim 24, further comprising applying in a second mode a current to the target tissue so as to thermally ablate cells of the target tissue.

* * * * *